United States Patent [19]

Ayling et al.

[11] Patent Number: 5,196,533

[45] Date of Patent: Mar. 23, 1993

[54] CYCLIZATION OF 5 AMINO-PYRIMIDINES TO QUINOID 6,6 DISUBSTITUTED DIHYDROPTERIDINES

[75] Inventors: June E. Ayling; Steven W. Bailey, both of Mobile, Ala.

[73] Assignee: South Alabama Medical Science Foundation, USA, Mobile, Ala.

[21] Appl. No.: 669,662

[22] Filed: Mar. 14, 1991

Related U.S. Application Data

[60] Division of Ser. No. 483,708, Apr. 11, 1983, abandoned, and a continuation of Ser. No. 910,327, Sep. 22, 1986, abandoned, and a continuation of Ser. No. 161,292, Feb. 18, 1988, abandoned.

[51] Int. Cl.$^5$ .......................................... C07D 475/04
[52] U.S. Cl. .................................... 544/118; 544/257; 544/258; 544/259; 544/260; 544/261; 544/122; 544/123; 544/251; 544/230; 544/296; 544/320; 530/331
[58] Field of Search ............... 544/258, 257, 259, 260, 544/118, 261; 514/249

[56] References Cited

U.S. PATENT DOCUMENTS

| | | | |
|---|---|---|---|
| 3,426,019 | 2/1969 | Pachter | 544/258 |
| 3,810,893 | 5/1974 | Wood | 544/258 |
| 4,665,182 | 5/1987 | Nichols | 544/258 |
| 4,937,342 | 6/1990 | Kurono et al. | 544/258 |

FOREIGN PATENT DOCUMENTS

| | | | |
|---|---|---|---|
| 0108890 | 5/1984 | European Pat. Off. | 544/258 |
| 84/04040 | 10/1984 | PCT Int'l Appl. | 514/249 |

OTHER PUBLICATIONS

Bailey et al. "Programme and Book of Abstracts" 7th Int'l. Symp. on Pteridines and Folic Acid Deriv. St. Andrews, Scotland p. 0.1 (1982).

Nair et al Jour. Med. Chem. vol. 17 No. 2 pp. 223-226 (1974).

Bailey et al. in Chem. & Bioc. of Pteridines de Gruyter Berlin-F.R.G., 1982, pp. 51-55.

Bailey et al. Biochemistry, 1983, vol. 22, pp. 1790-1798.

Lazarus et al. Biochemistry 1981 vol. 20 pp. 6834-6841.

Visconti et al. Liebig's Ann Chem. vol. 75, pp. 109-111 (1971).

Amarego et al. Aust. J. Chem. vol. 34, pp. 1921-1933 (1981).

*Primary Examiner*—Donald G. Daus

[57] ABSTRACT

6,6-Disubstituted pteridines which are useful for the regulation of enzymes are disclosed, along with a general method of synthesizing these compounds.

4 Claims, No Drawings

CYCLIZATION OF 5 AMINO-PYRIMIDINES TO QUINOID 6,6 DISUBSTITUTED DIHYDROPTERIDINES

This is a division of Ser. No. 6/483,708, filed Apr. 11, 1983, which was replaced with FWC #1, Ser. No. 910,327 filed Sep. 22, 1986 which was replaced with FWC #2, Ser. No. 07/161,292 filed Feb. 18, 1988 and abandoned Aug. 18, 1991.

TECHNICAL FIELD

The present invention relates to 6,6-disubstituted tetrahydropteridines and closely related compounds and to methods of synthesizing these compounds.

BACKGROUND ART

The pteridines utilized by higher animals fall mainly into two classes of pterin (2-amino-4-hydroxypteridine) enzyme cofactors, the derivatives of poly-gamma-glutamyltetrahydrofolates and tetrahydrobiopterin, although several pteridines diverging widely from the substitution patterns of these pterin series have significant roles in bacteria, plants, and insects. A common factor of several of the tetrahydropterin-utilizing enzymes is the oxidation of the pterin cofactor. For example, in the case of thymidylate synthetase (a major target of antifolate chemotherapy), the 5,10-methylene derivative of tetrahydrofolic acid is converted to 7,8-dihydrofolic acid. Likewise, the action of the three aromatic amino acid hydroxylases (phenylalanine, tyrosine, and tryptophan) yields a quinoid dihydrobiopterin of uncertain structure.

Catalysis by tyrosine hydroxylase is the rate limiting step in the biosynthesis of dopamine and norepinephrine. The activity of this enzyme in the caudate nucleus and substantia nigra is markedly lower in Parkinson's disease as is also the concentration of its cofactor tetrahydrobiopterin. Parkinson's disease is a debilitative disease which usually appears insidiously between 50 and 60 years of age. The disease is progressive, generally beginning with tremor followed by bradykinesia and rigidity. Estimates of the current number of cases of Parkinson's disease in the United States range between 500,000 and one million. Approximately one in 40 individuals will eventually become afflicted, creating about 50,000 new cases per year. A variety of anatomical and biochemical defects in the brains of Parkinson's patients have been noted, the most prominent involving the basal ganglia, with cell loss and depigmentation in the pars compacta of the substantia nigra. A large part of this lesion is due to degeneration of dopaminergic neurons in the nigro-striatal pathway.

A marked deficiency in dopamine concentration (less than 10% of normal, decreasing further with time after onset) is seen in striata of Parkinson's patients. Since its introduction in the mid-1960's, the use of L-dopa has become the major means of treatment. L-Dopa enters the brain via the aromatic amino acid transport system and is subsequently enzymatically decarboxylated to dopamine. Unfortunately, the action of peripheral decarboxylases normally convert about 95% of administered L-dopa rapidly to dopamine, which does not effectively permeate the blood-brain barrier. As a result, patients are frequently given a combination of carbidopa (a decarboxylase inhibitor) and L-dopa (Merck, Sharp and Dohme-Sinemet), thus reducing the total L-dopa required for optimal effect by about 75%.

Although L-dopa is generally considered the best available treatment for Parkinson's disease, a number of problems are encountered in its use. For example, between 15 and 25% of patients are totally unresponsive to any regime of L-dopa therapy. Furthermore, most patients cannot immediately tolerate the optimal dose and must be gradually titrated to an individual level. Even then, most experience nausea, especially during the initial phase of dosage increase. This adjustment period can be shortened to between 2 and 4 weeks by simultaneous use of carbidopa. The most serious common adverse reactions to L-dopa are abnormal involuntary movements and behavioral disturbances. Within the first 2 to 4 months of therapy about half of patients display choreiform or dystonic movements, increasing to about 80% of those on full dosage schedule for over a year. Serious mental side effects (psychotic episodes, depression and dementia) requiring reduction or withdrawal of the drug is seen in about 15% of cases. Although occasionally moderated by combination with carbidopa, many patients experience swings in ability of L-dopa to suppress bradykinesia (the "on-off" phenomenon).

The full benefit of L-dopa therapy generally lasts for only 2 to 4 years, followed by a decline in response. The effective duration or each dose decreases and akinesia paradoxica or "freezing" increases. Within 5 years the increasing side-effects usually begin to outweigh the remaining benefit of continued treatment. Since most Parkinson's patients live for 10 to 20 more year after onset of the disease, a need clearly still exists for a more effective and long lasting approach. A number of agents have been tested, either as modifiers of dopa therapy, or as dopaminergic agonists to replace L-dopa. At best, these approaches result in a trade-off between improvement of one side effect and the worsening of another. Accordingly, new methods of treating Parkinson's disease are needed.

Along these lines, several attempts have been made to increase cofactor concentration in the brain of patients having insufficient tyrosine hydroxylase activity and thus to increase the rate of tyrosine hydroxylation and dopa synthesis. Direct intraventricular infusion of tetrahydrobiopterin ($BH_4$) into rat brains caused a concommitant increase in catechols in the striatum with increase in brain concentration of tetrahydrobiopterin (Ketter et al., Nature, 249 476-478 (1974)). The effectiveness of $BH_4$ treatment has been suggested to be possibly even greater in Parkinson's patients, who have a two-fold lower than normal level of $BH_4$ in the cerebrospinal fluid (CSF) and four-fold lower in the brain (Lovenberg et al., Science, 204, 624-626 (1979)). However, peripherally administered tetrahydrobiopterin ($BH_4$) does not readily enter the brain. In the first experiments which demonstrated the poor ability of $BH_4$ to cross the blood brain barrier, 125 mg $BH_4$/kg body weight was injected intravenously into rats. $BH_4$ in the striatum was increased slightly and transiently, with a maximum increase of 30% in 15 mins, returning to normal in less than 2 hours. This is equivalent to 0.2% of the concentration administered assuming uniform body distribution. (Kettler et al., supra.)

After i.p. injection of $^{14}C$-$BH_4$ into rats, the isotope was detectable in all tissues analyzed (brain, kidney, liver, plasma, urine). Radioactivity peaked in the brain 1 hour after injection, at which time it was less than 1% of that found in plasma. $BH_4$ was lost from the plasma somewhat more rapidly than from the brain, but by 6 hours most of the radioactivity appeared in the urine as biopterin and its metabolites. Of the 64 μg of radioactive pterin injected per rat, about 10 ng (0.016%) reached the brain (Gal et al., *Neurochem. Res.*, 1 511-523 (1976)).

A comparison of oral and i.v. administration of BH₄ and other pterins has been made in humans, 1-5 years of age, with a genetic disorder in BH₄ biosynthesis. In addition to the neurological symptoms due to the inability of tyrosine and tryptophan hydroxylases to function in the absence of BH₄, these patients also have plasma phenylalanine levels 10 to 20 times normal, due to the requirement of liver phenylalanine hydroxylase for BH₄. It was found that doses of 2.5 mg BH₄/kg body weight administered by either route decreased the plasma phenylalanine levels to normal within 3-4 hours and maintained these low levels for 1-2 days. Dihydrobiopterin and sepiapterin, the presumed immediate precursors of BH₄ were as effective as BH₄ in lowering plasma phenylalanine when administered orally in doses of 2.5 mg/kg and 0.6 mg-1.25 mg/kg, respectively, and maintained normal levels of phenylalanine for 24 hours (Schaub et al., *Arch. Dis. Childhood*, 53, 674-683 (1978); Niederwieser et al., Lancet, 131-133 (1979); Curtius et al., *Clin. Chim. Acta*, 93, 251-262 (1979)). Therefore, oral administration of biopterin analogues appears to be equally as effective as i.v. administration.

The ability of BH₄ to enter the brain has been studied in BH₄ deficient patients. After 2 mg BH₄ (i.v.)/kg/day for 3 days in a 1-2 yr old, 15-kg body weight, BH₄-synthesis-deficient child, no increase in CSF BH₄ was detected 1 day after the last injection. Analysis of CSF at this time for dopamine and serotonin metabolites showed a slight increase in homovanillic acid from 29 to 44 ng/ml (normal=130 ng/ml) and in hydroxyindoles from 92 to 147 ng/ml, indicating that a trace of BH₄ had penetrated the brain (Danks et al., *Pediat. Res.*, 13, 1150-1155 (1979)).

At doses <2.5 mg BH₄/kg body weight there is insufficient penetration of BH₄ into the brain to have any effect on the neurological symptoms (ptosis, ataxia) displayed by BH₄ deficient patients. However, at higher doses, up to 22 mg BH₄ (p.o.)/kg, alleviation of the symptoms has been demonstrated in two patients. With one of these patients, sepiapterin was shown to have an effect at 2.75 mg (p.o.)/kg (Niederwieser et al., *Eur. J. Pediatr.*, 138, 110-112 (1982)). Studies with the other patients demonstrated an increase in CSF BH₄ from 2 ng to 44 ng/ml 2.5 hours after oral treatment at a dose of 20 ng/BH₄/kg/day (administered in two equal doses at 12 hr intervals). This is 0.22% of that which would be expected assuming uniform body distribution and retention and is close to that noted above in rat brain 1.5 hrs after i.p. injection of 30 mg/kg (Kaufman et al., *Pediatrics*, 70, 376-380 (1982)).

Currently 6-methyltetrahydropterin (6-MePH₄) is the only other tetrahydropterin that has been studied by direct analysis for its ability to enter the brain. In rats, administration of 6-MePH₄ to rats, 0.11 μmole (i.p.)/gm body weight, demonstrated that this pterin entered the brain up to 10 times more efficiently than an equal dose of BH₄. Levels of 2 nmoles/g brain were reached (i.e., 2% of that expected assuming equal body distribution) at 30 minutes and were maintained until 2 hours after injection. The half life for retention by the brain was 3 hrs. The blood level was 40 μM at 30 minutes and had dropped to 10 μM by 2 hrs, the half life for retention by the plasma being 0.7 hours. In one experiment, enzymatic analysis demonstrated that over 85% of striatal 6-MePH₄ remained in the fully reduced tetrahydroform 2 hrs after injection (Kapatos and Kaufman, *Science*, 212, 955-956 (1981)). However, similar experiments by experimenters who claim the use of more reliable assay techniques indicate that only 30% of the 6-MePH₄ in the brain was in the reduced form (Curtius et al., in *Pteridines and Folic Acid Derivatives*, Blair, ed., Walter de Gruyter, Berlin, 1982).

The effectiveness of 6-MePH₄ has been tested in one human patient with inherited deficiency of BH₄ biosynthesis. Three hours after an intravenous injection of 20 mg 6-MePH₄/kg body weight, the CSF level was 0.45 μg/ml (i.e., 2.2% of that expected on the basis of equal body distribution), dropping to 0.06 μg/ml at 9.5 hours. Two hours after a dose of 8 mg/kg, CSF homovanillic acid increased from 9 to 22 ng/ml (normal-132 ng/ml for 2-4 yrs of age), and 5-hydroxyindoleacetic acid increased from 6 to 18 ng/ml (normal=30 ng/ml for 2-4 yrs of age). Similar improvements in clinical symptoms were observed as with BH₄ treatment. (Kaufman et al., (1982), supra).

Another problem associated with the use of tetrahydrobiopterin as its instability. As shown in the following scheme, during hydroxylation BH₄ is oxidized to quinoid dihydrobiopterin (BH₂) which is then reduced back to BH₄ in the presence of NADH and dihydropteridine reductase. The nonenzymatic oxidation of tetrahydropterins by molecular oxygen, a generally rapid process in neutral or alkaline aqueous media, also initially generates the quinoid dihydroform. The quinoid BH₂ form is unstable and in the absence of a reducing system rearranges to 7,8-dihydrobiopterin with a half-life of only a few minutes under physiological conditions. This latter tautomer is not a substrate for dihydropteridine reductase.

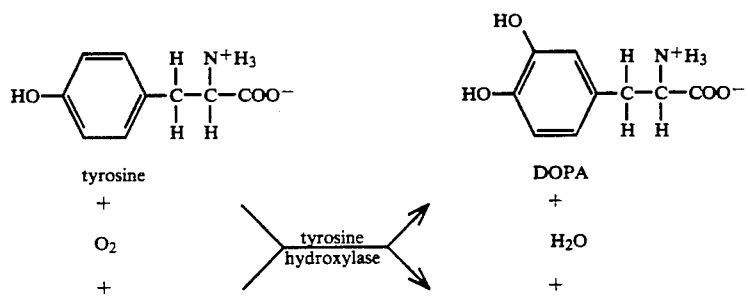

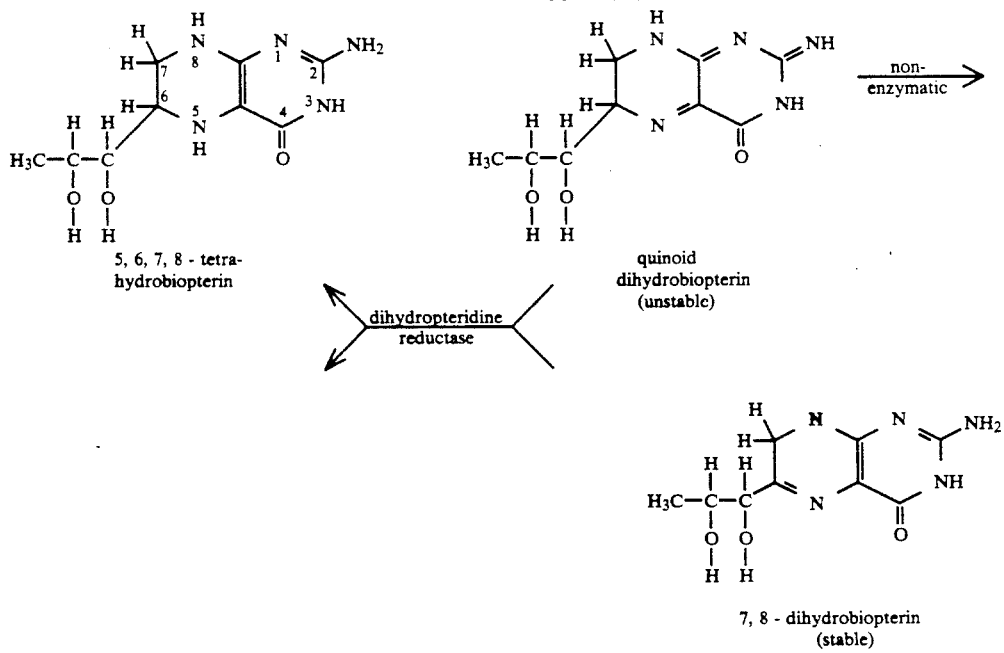

5, 6, 7, 8 - tetra-hydrobiopterin quinoid dihydrobiopterin (unstable)

7, 8 - dihydrobiopterin (stable)

As will become clearer when the present invention is more fully disclosed, the present invention relates to 6,6-disubstituted tetrahydropteridines and related compounds in the treatment of Parkinson's disease and other disorders that would benefit from activation of aromatic aminoacid hydroxylases. Although some 6,6-disubstituted tetrahydropteridines have previously been synthesized for chemical studies, their use and their advantages for such treatments do not appear to have been previously recognized.

The first synthesis of 6,6-disubstituted tetrahydropteridines utilized nucleophilic addition of cyanide across the 7,8 double bond of 6-methyl-7,8-dihydropterin, yielding 6-cyano-6-methyltetrahydropterin (Viscontini et al., Helv. Chim. Acta, 54, 811–818 (1971)). After a number of intermediate steps, the nitrile was reduced and the final compound, 6-aminomethyl-6-methyl-5,6,7,8-tetrahydropterin, was obtained. This molecule proved to be less stable than expected, since upon oxidation the resulting quinoid dihydropterin was able to reform the starting 6-methyl-7,8-dihydropterin by loss of the amino methyl group as ammonia and formaldehyde.

Recently the above approach has been extended to the synthesis of 6,6-dimethyltetrahydropterin by reaction of methyllithium with trimethylsilylated 6-methyl-7,8-dihydropterin followed by desilylation (Armarego and Waring, Aust. J. Chem., 34, 1921–1933 (1981)). A yield of 28% was reported, but evaluation of the ultraviolet absorbance characteristics indicates that it was only 82% pure. Although this method is relatively straightforward, two potential disadvantages are envisioned. First, a chromatography step is required in order to liberate the relatively low yield of desired material from by-products, a process that would inhibit scale up. More importantly, it is doubtful that this procedure has a wide scope, for although a number of 7,8-dihydropterins monosubstituted at position 6 are potentially available by current procedures, it seems likely that yield will further suffer with increasing hindrance of C(6) by groups larger than methyl.

Although many procedures are known for the synthesis of pteridines, the only known prior art relevant to the overall synthetic method of the present invention can be found in a publication of Lazarus et al., Biochemistry, 20, 6834–6841 (1981). The purpose of the relevant part of this work was to determine whether 2,5-diamino-6-(meso-1-methyl-2-aminopropylamino)-4-pyrimidinone could be oxidatively cyclized to fully oxidized 6,7-dimethylpterin. Nowhere in this work is it stated or implied that the procedure is a general method of pteridine synthesis. Further, the potential application to the synthesis of 6,6-disubstituted tetrahydropteridines is nowhere discussed, since the main thrust of the article is toward preparing a fully oxidized pterin, which would not be possible with disubstitution at a single ring position. Nor is the use of such compounds for the treatment of Parkinson's disease or other diseases involving pterin cofactors discussed in this or any of the other references which disclose 6,6-disubstituted pterins.

Accordingly, prior to the present invention, there remained a great need for an improved method of regulating enzymes having tetrahydropterin cofactors.

DISCLOSURE OF THE INVENTION

Accordingly, it is an object of this invention to provide a stable compound useful for the treatment of Parkinson's disease and other disorders involving aromatic amino acid hydroxylation enzymes.

It is a further object of this invention to provide a method specifically for treating Parkinson's disease.

It is another object of this invention to provide a method of inhibiting thymidylate synthetase at its cofactor binding site.

It is yet another object of this invention to provide a method of treating diseases caused by genetic deficiencies in the synthesis of biopterin and tetrahydrobiopterin.

It is a still further object of this invention to provide a general method of synthesizing 6,6-disubstituted tetrahydropteridines.

These and other objects of the invention as will hereinafter become more readily apparent have been accomplished by providing a method of activating an aromatic amino acid hydroxylase, comprising:

administering to a human or animal in need of said activating an amount effective to increase the activity of said enzyme of a compound of the formula:

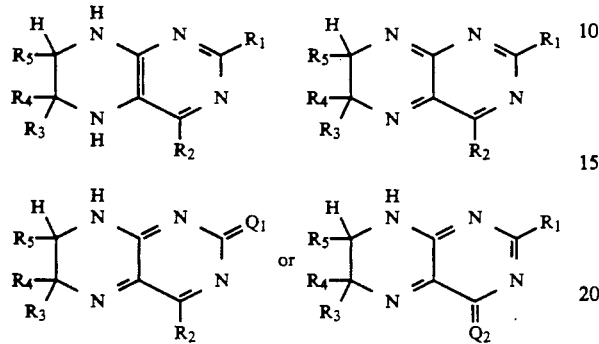

wherein $R_1$ and $R_2$ are the same or different and represent (1) hydroxy;
(2) alkoxy of 1 to 4 carbon atoms;
(3) amino of the formula —$NR_6R_7$, wherein $R_6$ and $R_7$ are the same or different and represent
  (a) hydrogen;
  (b) alkyl of 1 to 4 carbon atoms; or
  (c) cycloalkyl of 3 to 6 carbon atoms;
(4) cycloamino selected from the group consisting of
  (a) aziridino,
  (b) azetidino,
  (c) pyrrolidino,
  (d) piperidino, and
  (e) morpholino, wherein said cycloamino is attached to the pyrimidine ring of the formula through a nitrogen of the cycloamino; or
(5) alkylthio of 1 to 3 carbons;

$R_3$ and $R_4$ are the same or different and represent
(1) alkyl of 1 to 12 carbon atoms;
(2) alkenyl of 2 to 7 carbon atoms;
(3) alkynyl of 2 to 7 carbon atoms;
(4) cycloalkyl, saturated or unsaturated, of 3 to 10 carbon atoms with 3 to 7 atoms in the ring;
(5) bicycloalkyl, saturated or unsaturated, of 6 to 13 carbon atoms with 4 to 7 atoms per ring;
(6) adamantyl;
(7) alkyl of 1 to 12 carbon atoms or alkenyl of 2 to 7 carbon atoms, substituted with 1, 2, 3 or 4 of hydroxy, oxo, thio, phosphate, fluoro, chloro, or bromo;
(8) fluoro, chloro;
(9) amino;
(10) aziridino attached to carbon 6 of said formula through nitrogen or a carbon;
(11) aryl, wherein aryl is phenyl or naphthyl;
(12) arylalkyl of 7 to 13 carbon atoms;
(13) aryl or arylalkyl substituted with 1,2, or 3 alkyl of 1 to 4 carbon atoms, trifluoromethyl, hydroxy, alkoxy of 1 to 4 carbon atoms, fluoro, chloro, bromo, amino, methylamino, or dimethylamino in the aryl group;
(14) thienyl, thienylmethyl;
(15) furyl, furylmethyl;
(16) tetrahydrofuryl;
(17) pyridyl, pyridylmethyl;
(18) pyridyl substituted with 1, 2, or 3 alkyl of 1 to 4 carbon atoms, amino, hydroxy, chloro, or fluoro;
(19) deuterium;
(20)

wherein $R_{12}$ is a 1- to 22- carbon alkyl or alkenyl group; or
(21) carboxyl; and $R_5$ represents
(1) hydrogen,
(2) alkyl of one to 6 carbon atoms,
(3) cycloalkyl of 3 to 7 carbon atoms,
(4) phenyl, phenylmethyl,
(5) hydroxyl,
(6) alkoxy of 1 to 4 carbon atoms,
(7) amino, or
(8) carboxyl; and $Q_1$ and $Q_2$ independently represent O or $NR_6$; with the provisions that $R_3$ and $R_4$ together may form a 3 to 7 carbon spiro alkyl ring, with carbon 6 of the pteridine ring being the spiro carbon; or $R_4$ and $R_5$ together may form a 5- or 6-membered carbocyclic ring fused to pteridine carbons 6 and 7.

Likewise, certain compounds of the invention can be used as inhibitors of thymidylate synthetase, especially those of the formula:

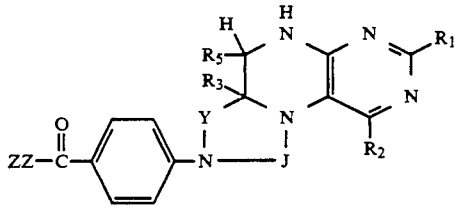

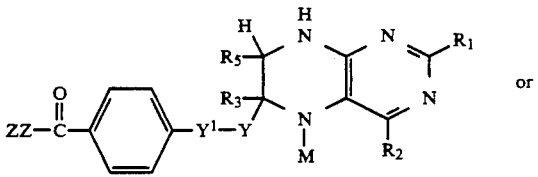

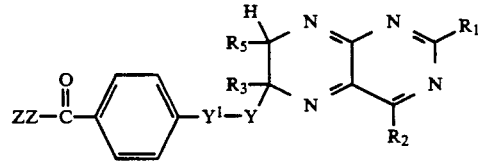

wherein Y is methylene or ethylene either of which is unsubstituted or is substituted with 1 or 2 substituents selected from the group consisting of fluoro, chloro, and methyl;

Y' is
(a) —$NR_{10}$—, wherein $R_{10}$ is hydrogen; formyl; formimino; hydroxymethyl; benzyl; or an alkyl, alkenyl, or alkynyl of 1 to 3 carbon atoms,
(b) —$CH_2$—, —$CHCH_3$—, —$C(CH_3)_2$—, or —$CH(C_2H_5)$—,
(c) —O—, or
(d) —S—;

ZZ represents the residue of an amino acid or amino acid polymer of the formula

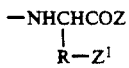

wherein Z represents OH, $C_1$–$C_4$ alkyloxy, or $NH_2$, R represents a divalent alkyl radical of 1 to 5 carbons, and $Z^1$ represents $NH_2$ or $COZ^2$ where $Z^2$ is Z or the residue of an amino acid or amino acid polymer of the formula

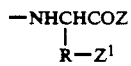

wherein the total number of amino acid residues in ZZ does not exceed 7 and each Z, R, $Z^1$, and $Z^2$ operates independently in defining ZZ;

M is alkyl, alkenyl or alkynyl of 1 to 3 carbon atoms, formyl, fomimino, benzyl, hydrogen, or hydroxymethyl; and J is —$CH_2$—, —$CH_2CH_2$—, or =CH—, where the single bond of =CH— is attached to N5; and the remaining substituents have the meanings previously given with the proviso that $R_1$ or $R_2$ may additionally represent thio or hydrogen and $R_3$ may not be deuterium.

Many 6,6-disubstituted tetrahydro- and dihydropteridine compounds were not known to be useful for the methods described herein or for any other use and had never been synthesized or contemplated by others, and such compounds themselves are also encompassed by the present invention.

Likewise, a general method of synthesis for the compounds described above is also part of the present invention. This process comprises oxidizing a 6-(2-amino-2,2-disubstituted-ethylamino)-5-aminopyrimidine to an imine and hydrolyzing said imine, whereby condensation takes place to give a 6,6-disubstituted dihydropteridine.

BEST MODE FOR CARRYING OUT THE INVENTION

The present invention provides an improved method of regulating enzymes which use tetrahydropterins as cofactors by providing the cofactor in a form which is more stable than naturally occurring 6-monosubstituted forms. As is discussed in the introductory section, the oxidation of the tetrahydropterin, either by participation in an enzymatically catalyzed reaction or nonenzymatically by interaction with molecular oxygen, yields initially a quinoidal dihydropterin. Quinoid dihydropterins which are monosubstituted at position 6 are unstable and rapidly rearrange to 7,8-dihydropterins. The latter tautomeric form is not a substrate for dihydropteridine reductase and therefore can no longer be reduced back to the active form of the cofactor. The various reports discussed in the background section indicate that although 6-methyltetrahydropterin enters rat brain at a faster rate than tetrahydrobiopterin, a significant percentage of the former is found in the oxidized nonfunctional state. This drawback is prevented by 6,6-disubstitution. An additional advantage (as an inhibitor) exists for cofactors of thymidylate synthetase, as is discussed in a later section.

It was previously known that the rate limiting step in the conversion of quinoid dihydropterins to 7,8-dihydropterins is loss of hydrogen from position-6 (Archer and Scrimgeour, Can. J. Biochem., 48, 278–287, (1970)). However, no suggestion was made that replacing the hydrogen at position-6 would provide longer acting cofactors in vivo. This principle is demonstrated in the present application by a quinoid 6,6-disubstituted dihydropterin which is shown to be between one and two orders of magnitude more stable than monosubstituted quinoid dihydropterins. 6,6-Substituted quinoid-dihydropterin can be reduced both by dihydropteridine reductase and nonenzymatically by endogenous reduced pyridine nucleotides and thiols to a tetrahydropterin that is shown to be a cofactor for both rat liver phenylalanine hydroxylase and rate and bovine striatal tyrosine hydroxylase.

Many 6,6-disubstituted tetrahydropteridines are useful as cofactors according to the method of the present invention. For example, the three aromatic amino acid hydroxylases (phenylalanine, tyrosine and tryptophan hydroxylase) each utilize the cofactor tetrahydrobiopterin and molecular oxygen to introduce a hydroxyl group into an aromatic ring. Tetrahydrobiopterin therefore performs a similar function with each enzyme. Due to this similarity, determination of which types of substitution patterns are useful can be based on studies not only with brain tyrosine hydroxylase but also with tyrosine hydroxylase from adrenal and phenylalanine hydroxylase from liver, since more data are available with the latter two enzymes. The following paragraphs discuss the possible substituents at the various positions of a pteridine. For the purpose of this discussion, the positions are numbered as shown in the following formula, which uses the standard numbering system for pteridines:

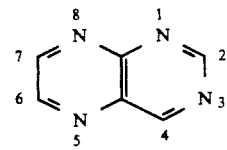

It should be noted that the numbers of the standard positions do not correspond with the numbers of the substituents given in the present claims, which are numbered sequentially in the order of discussion for clarity rather than being numbered according to this standard system which would have resulted in a claim substituent pattern having gaps.

Positions 2 and 4: To retain cofactor activity an electron donating group is required at both positions. With phenylalanine hydroxylase: H at either the 2- or 4-position allows binding, but cofactor activity is lost; SH at the 4-position allows binding, but not cofactor activity; $NH_2$ at this position prevents binding. A hydroxyl at position-2 prevents binding to both phenylalanine hydroxylase and adrenal tyrosine hydroxylase. 2-Methylamino is active with phenylalanine hydroxylase, but 2-dimethylamino is not, even though it has appropriate electron donating properties. A number of monoalkyl-, dialkyl-, and cycloalkyl-amino substituents are possible for position 2, with the expectation that one or more patterns may confer specificity for tyrosine hydroxylase in the basal ganglia. Both central nervous system and peripheral side-effects may be minimized if only the target hydroxylase is stimulated and not phenylalanine, tryptophan, or adrenal-tyrosine hydroxylases. Although such specificity maybe desirable, it does not appear to be an absolute requirement, as judged from the effectiveness of 6-methyl-tetrahydropterin and tetrahydrobiopterin in similar treatments. A selective affinity for tyrosine hydroxylase might also be obtained from substitution patterns at positions 6 and/or 7.

Position 7: Significant modifications of enzyme kinetic parameters have been observed in all three aromatic amino acid hydroxylases by substitution of position 7 with a methyl group. In most cases this leads to a cofactor that decreases the maximum velocity of hydroxylation and increases the Km's for cofactor and substrates. Specific to tyrosine hydroxylase is the observation that a 7-methyl group induces a partially uncoupled reaction (more than one molecule of cofactor is consumed per molecule of dopa generated). While these effects are in general opposed to the desired properties, it may be possible to influence selectivity by the choice of an alternative group.

Position 6: It is most likely that the majority of pharmacologically desirable properties of a tyrosine hydroxylase cofactor will be obtained by optimization of the substituents at position 6. This is due to the observations that (a) both phenylalanine and tyrosine hydroxylases can accept a relatively large variety of groups at this position and (b) substantial modification of the kinetic parameters of both enzymes is promoted by the nature of the group. The influences of substitution pattern on optimization of properties promoting an effective drug include the following:

(1) The dosage required to achieve a useful response will be lowered as the cofactor analog elicits the following enzyme kinetic parameters: high maximum velocity ($V_{max}$) and low Michaelis-constants (Km) for tyrosine, oxygen and cofactor analog itself. Furthermore, retention of feedback inhibition by catecholamines that approximates the functioning of normal brain would encourage a uniform response as the concentration of drug in the brain changes. With adrenal tyrosine hydroxylase only a slight effect on $V_{max}$ and cofactor Km is observed when the 1-erythrodihydroxypropyl group of tetrahydrobiopterin is exchanged for a methyl group. In contrast, the Km's for both tyrosine and oxygen, and the Ki for dopa are all greatly increased. Modification of the stereochemistry of the dihydroxypropyl group or the chirality at carbon 6 has intermediate effects in comparison to replacement by a methyl. With striatal tyrosine hydroxylase, a single phenyl substituent at position 6 stimulates a higher $V_{max}$ and a lower cofactor Km than tetrahydrobiopterin. Disubstitution at C-6 with two methyl groups or with a methyl and a phenyl results in a $V_{max}$ to cofactor Km ratio similar to that with the 6-monomethyltetrahydropterin and superior to that of tetrahydrobiopterin. It is therefore possible to maintain desired enzyme kinetic parameters while at the same time blocking tautomeric rearrangement, for example with a methyl.

(2) The rate of transport of a drug across the blood-brain barrier and the concentration finally achieved in the brain for a given level in the peripheral circulation is directly related to dosage requirement. An increase in drug hydrophobicity is a means of promoting rapid equilibration through membranes. Although this increase may in part be obtained by alkylation of the 2-amino group, the position most likely able to carry a bulky substituent without deleterious changes in cofactor properties is position 6 as exemplified above by 6-phenyltetrahydropterin. However, 6-phenyltetrahydropterin itself is not a likely candidate for the treatment of Parkinson's disease, since as a result of the electron withdrawing phenyl ring the quinoid dihyropterin is highly unstable and very rapidly tautomerizes to the inactive 7,8-dihydropterin.

(3) That selectivity between two hydroxylases is possible is indicated by a comparison of phenylalanine hydroxylase with striatal tyrosine hydroxylase in their responses to tetrahydrobiopterin and 6-phenyltetrahydropterin. With the latter enzyme, 6-phenyltetrahydropterin increases $V_{max}$ 10-fold, whereas with phenylalanine hydroxylase it decreases $V_{max}$ 10-fold compared to tetrahydrobiopterin (Bailey and Ayling, Biochem. Biophys. Res. Comm., 95, 1614–1621 (1978)).

(4) Although quinoid 6,6-dimethyldihydropterin is one to two orders of magnitude more stable than the quinoid forms of 6-methyldihydropterin or dihydrobiopterin, even greater stability may increase the effective duration of a single dose. The degradation of quinoid 6,6-dimethyldihydropterin appears to be due to an initial hydration across the C4a-5N bond followed by ring rearrangement. Substitution of one or both 6-carbon positions with hydrophobic groups is believed to protect against this hydration by restricting the access of water to the nearby susceptible bond. This approach to increased stability may be compatible with several of the above goals, especially improvement of transport by hydrophobic groups.

Taking these factors into consideration, the present invention involves a method of activating an aromatic amino acid hydroxylase enzyme in a human or animal, which comprises administering to a human or animal in need of said activating an effective amount of a compound of the formula

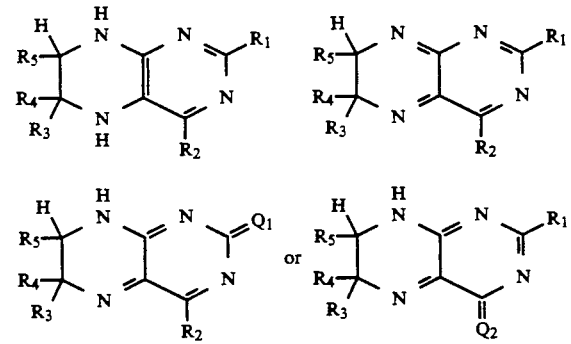

where the substituents have the meanings previously given in the Disclosure of the Invention section for aromatic amino acid hydroxylase activators.

Certain of these compounds and substituents are preferred for use in activating an aromatic amino acid hydroxylase. When the substituents are considered individually as they may be for the purposes of this invention in defining groups of preferred compounds (either as compounds per se or for use with this method of the invention), $R_1$ is preferably amino, alkylamino of 1 to 3 carbons (especially methylamino), alkoxy of 1 or 2 carbons (especially methoxy), dialkylamino wherein each alkyl has 1 or 2 carbons, cycloalkylamino having 1 nitrogen and a total of 3, 4, 5 or 6 atoms in the ring, or morpholino, more preferably is amino or alkylamino of 1 to 3 carbons, and most preferably is amino; $R_2$ is preferably hydroxy and must be hydroxy if $R_1$ is alkoxy or dialkylamino; $R_3$ is preferably methyl, fluoro, deuterium, or trifluoromethyl, more preferably methyl, fluoro, or deuterium, and most preferably is methyl; $R_4$ is preferably alkyl of 1-8 carbons, alkyl of 1-6 carbons substituted with 1 or 2 hydroxy, phenyl, phenylmethyl, phenylethyl, phenylpropyl, cycloalkyl of 3 to 6 carbons, cyclohexylmethyl, or cyclohexylethyl (with the provisions that any named phenyl or phenylalkyl may be substituted with 1 or 2 halogen atoms, especially fluorine or chlorine, and that if $R_4$ is phenyl, $R_3$ is a preferred group other than deuterium); $R_5$ is preferably hydrogen, methyl, or deuterium with hydrogen being more preferred; spiro $R_3$ and $R_4$ is preferably spiropropyl, spirobutyl, spiropentyl, or spirohexyl; and fused $R_4$ and $R_5$ is preferably cyclobutyl, cyclopentyl, or cyclohexyl with cyclopentyl or cyclohexyl being more preferred. Preferred compounds are defined by selecting one or more of these listings of preferred substituents in combination with a general formula previously given.

Certain combinations of substituents are also especially preferred. One preferred grouping occurs when $R_1$ is amino, $R_2$ is hydroxy, $R_3$ is methyl, fluoro, or deuterium, $R_5$ is hydrogen, and $R_4$ is selected from the previous list of preferred substituents.

Preferred compounds for use with the aspect of the invention involving the activating of aromatic amino acid hydroxylase enzymes include the following compounds having the formula as shown below:

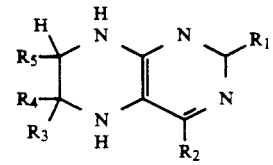

| Compound | $R_1$ | $R_2$ | $R_3$ | $R_4$ | $R_5$ |
| --- | --- | --- | --- | --- | --- |
| 1 | NH$_2$ | OH | CH$_3$ | Methyl | H |
| 2 | " | " | " | Ethyl | " |
| 3 | " | " | " | n-Propyl | " |
| 4 | " | " | " | i-Propyl | " |
| 5 | " | " | " | Cyclopropyl | " |
| 6 | " | " | " | n-Butyl | " |
| 7 | " | " | " | 2-Methylpropyl | " |
| 8 | " | " | " | 1-Methylpropyl | " |
| 9 | " | " | " | Cyclobutyl | " |
| 10 | " | " | " | n-Pentyl | " |
| 11 | " | " | " | 1-Methylbutyl | " |
| 12 | " | " | " | 2-Methylbutyl | " |
| 13 | " | " | " | 3-Methylbutyl | " |
| 14 | " | " | " | 1-Ethylpropyl | " |
| 15 | " | " | " | 2,2-Dimethylpropyl | " |
| 16 | " | " | " | 1,1-Dimethylpropyl | " |
| 17 | " | " | " | Cyclopentyl | " |
| 18 | " | " | " | n-Hexyl | " |
| 19 | " | " | " | 1-Methylpentyl | " |
| 20 | " | " | " | 2-Methylpentyl | " |
| 21 | " | " | " | 3-Methylpentyl | " |
| 22 | " | " | " | 4-Methylpentyl | " |
| 23 | " | " | " | 1-Ethylbutyl | " |
| 24 | " | " | " | 1-Cyclohexyl | " |
| 25 | " | " | " | 1,1-Dimethylbutyl | " |
| 26 | " | " | " | n-Heptyl | " |
| 27 | " | " | " | 1-Methylhexyl | " |
| 28 | " | " | " | Cyclohexylmethyl | " |
| 29 | " | " | " | n-Octyl | " |
| 30 | " | " | " | 1-Cyclohexylethyl | " |
| 31 | " | " | " | 1-Methylheptyl | " |
| 32 | " | " | " | 2-Cyclohexylethyl | " |
| 33 | " | " | " | 1-Hydroxyethyl | " |
| 34 | " | " | " | 2-Hydroxyethyl | " |
| 35 | " | " | " | 1-Hydroxypropyl | " |
| 36 | " | " | " | 2-Hydroxypropyl | " |
| 37 | " | " | " | 1,2-Dihydroxyethyl | " |
| 38 | " | " | " | 1,2-Dihydroxypropyl | " |
| 39 | " | " | " | 1-Hydroxybutyl | " |
| 40 | " | " | " | 2-Hydroxybutyl | " |
| 41 | " | " | " | 1,2-Dihydroxybutyl | " |
| 42 | " | " | " | 1-Hydroxypentyl | " |
| 43 | " | " | " | 2-Hydroxypentyl | " |
| 44 | " | " | " | 1,2-Dihydroxypentyl | " |
| 45 | " | " | " | 1-Hydroxyhexyl | " |
| 46 | " | " | " | 2-Hydroxyhexyl | " |
| 47 | " | " | " | 1,2-Dihydroxyhexyl | " |
| 48 | " | " | " | Phenylmethyl | " |
| 49 | " | " | " | 2-Phenylethyl | " |
| 50 | " | " | " | 3-Phenylpropyl | " |
| 51 | " | " | " | Phenyl | " |
| 52-101 | " | " | D | Same as 1-50 | " |
| 102-152 | " | " | F | Same as 1-51 | " |
| 153-203 | " | " | CF$_3$ | Same as 1-51 | " |
| | | | | $R_3$ and $R_4$ taken together | |
| 204 | NH$_2$ | OH | | 6-spiropropyl | " |

-continued

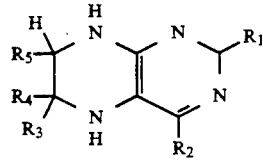

| Compound | R₁ | R₂ | R₃ | R₄ | R₅ |
|---|---|---|---|---|---|
| 205 | " | " | | 6-spirobutyl | " |
| 206 | " | " | | 6-spiropentyl | " |
| 207 | " | " | | 6-spirohexyl | " |
| | | | | R₄ and R₅ taken together | |
| 208 | " | " | CH₃ | 6,7-dimethylene | |
| 209 | " | " | " | 6,7-trimethylene | |
| 210 | " | " | " | 6,7-tetramethylene | |
| 211 | " | " | D | 6,7-dimethylene | |
| 212 | " | " | " | 6,7-trimethylene | |
| 213 | " | " | " | 6,7-tetramethylene | |
| 214–426 | NHCH₃ | " | (⟵——As for 1–213——⟶) | | |
| 427–639 | NHC₂H₅ | " | (⟵——As for 1–213——⟶) | | |
| 640–852 | NH(CH₂)₂CH₃ | " | (⟵——As for 1–213——⟶) | | |
| 853–1065 | NHCH(CH₃)₂ | " | (⟵——As for 1–213——⟶) | | |

Turning now to another preferred embodiment of the invention, 6,6-disubstituted pteridines can be used as inhibitors to regulate the enzyme thymidylate synthetase. Thymidylate synthetase catalyzes the methylation of deoxyuridine monophosphate (dUMP) to form deoxythymidine monophosphate (dTMP), an essential precursor of DNA synthesis. Inhibitors of thymidylate synthetase are cytotoxic and therefore may be used to combat bacterial, fungal, or parasitic infections, as well as neoplastic growth (Danenberg, Biochem. Biophys. Acta, 473, 73–82 (1977), which is herein incorporated by reference). Uracil derivatives, e.g., 5-fluorouracil, have been used extensively as inhibitors of thymidylate synthetase. These compounds are converted, in vivo, to deoxyuridine monophosphate analogs, which inhibit thymidylate synthetase by competing with the substrate, dUMP. The other substrate required by the enzyme, $N^5,N^{10}$-methylenetetrahydrofolic acid, serves as the source of the methyl group, which is derived from the $N^5,N^{10}$-methylene and the hydrogen at C-6 of the pteridine ring. Another series of analogs which inhibit thymidylate synthetase, therefore, comprises derivatives and analogs of tetrahydrofolic acid. Thymidylate synthetase is the only known enzyme for which the hydrogen at the 6-position of the pteridine ring is essential for activity. Substitution of this position with a small group, e.g., methyl or fluoro, should have little effect on binding but will completely block activity, thus providing a highly specific inhibitor of thymidylate synthetase.

Accordingly, the present invention also involves a method of inhibiting thymidylate synthetase in a human or animal, which comprises administering to a human or animal in need of said inhibiting an effective amount of a compound of the formula

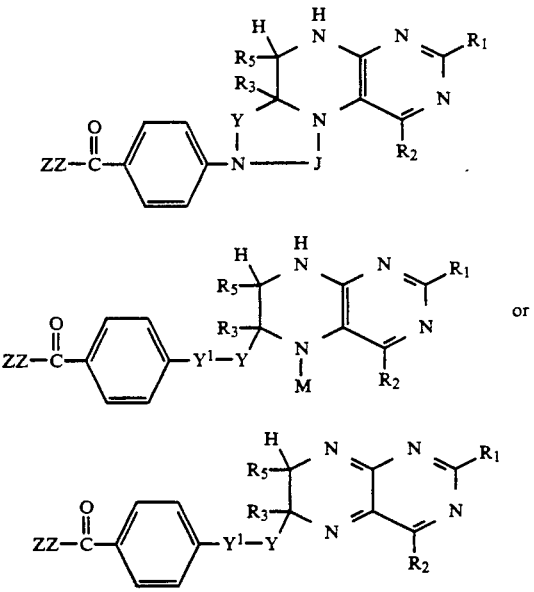

where the substituents have the meanings previously given in the Summary of the Invention section for thymidylate synthetase inhibitors.

A human or animal in need of said inhibiting is one infected with a bacterium, fungus, or parasite or one which is suffering from a neoplastic growth. Since DNA synthesis is inhibited, rapidly growing cells and microorganisms are inhibited to a greater extent than normal cells as is well-known in the art. Thus, "inhibiting thymidylate synthetase in a human or animal" refers both to inhibition of enzyme in the rapidly growing neoplastic cells of the human or animal being treated and to inhibition of enzyme in cells of microorganisms which are themselves present in the human or animal being treated.

When the substituents are considered individually as they may be for the purposes of this invention in defining groups of preferred compounds (either as compounds per se or for use with this method of the invention), $R_1$ is preferably amino, hydrogen, hydroxy, thio, alkoxy of 1 or 2 carbons (especially methoxy), alkylamino of 1 or 2 carbons (especially methylamino), or alkylthio of 1 or 2 carbons (especially methylthio) and more preferably is amino; $R_2$ is hydroxy, amino, thio, alkoxy of 1 or 2 carbons (especially methoxy), hydrogen, alkylamino of 1 or 2 carbons (especially methylamino), or alkylthio of 1 or 2 carbons (especially methylthio) and more preferably is hydroxy; $R_3$ is preferably methyl, ethyl, ethenyl, ethynyl, fluoro, amino, aminomethyl, carboxyl, or methyl substituted with hydroxy or fluoro, more preferably is methyl, ethyl, or fluoro, and most preferably is methyl; $R_5$ is preferably hydrogen, methyl, hydroxy, ethyl, or phenyl and more preferably is hydrogen; Y is preferably —CH$_2$—, —CH$_2$CH$_2$—, —CHF—, —CH(CH$_3$)—, —CHCl—, or —CF$_2$— and more preferably is —CH$_2$— or —CH$_2$CH$_2$—; Y' is preferably —NH—, —N(CH$_3$)—,

—CH$_2$—, —CH(CH$_3$)—, —CH(C$_2$H$_5$)—, —O—, —S—, or —C(CH$_3$)$_2$—, is more preferably —NH—, —N(CH$_3$)—,

—CH$_2$—, —CH(CH$_3$)—, or —CH(C$_2$H$_5$)—, and most preferably is —NH—, —N(CH$_3$)—, or

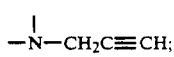

RZ$^1$ is preferably —CH$_2$CO$_2$H, —CH$_2$CH$_2$CO$_2$H, or —(CH$_2$)$_4$NH$_2$ and more preferably is —CH$_2$CH$_2$CO$_2$H; Z and Z$^2$ are preferably OH; M is preferably hydrogen, formyl, methyl, formimino, or hydroxymethyl, more preferably is hydrogen, formyl, or methyl, and most preferably is hydrogen; J is preferably —CH$_2$—; and ZZ preferably consists of one amino acid residue. Preferred groupings of compounds are defined by selecting one or more of these listings of preferred substituents in combination with a general formula previously given.

Certain combinations of substituents are also especially preferred. One preferred grouping occurs when $R_1$ is amino, methylamino, or hydroxy, $R_2$ is hydroxy or amino, $R_3$ is methyl, ethyl, ethenyl, ethynyl or fluoro, $R_5$ is hydrogen, and the remaining substituents are selected from the preferred groups given above. Especially preferred for use as thymidylate synthetase inhibitors are compounds in which $R_1$ is amino, $R_2$ is hydroxy, $R_3$ is fluoro, methyl, or ethyl, and $R_5$ is hydrogen. Of these, the compounds in which a methylene bridge joins N5 to the substituent on C6 are particularly preferred.

Preferred compounds for use with the aspect of this invention involving the inhibition of thymidylate synthetase include compounds having the formula

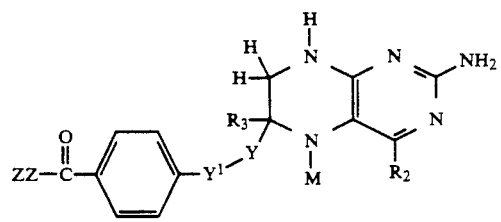

wherein the substituents are as follows:

| Compound | $R_2$ | $R_3$ | Y | Y' | M | ZZ |
|---|---|---|---|---|---|---|
| 1 | OH | F | CH$_2$ | NH | H | glu |
| 2 | " | CH$_3$ | " | " | " | " |
| 3 | " | C$_2$H$_5$ | " | " | " | " |
| 4 | " | F | CH$_2$CH$_2$ | " | " | " |
| 5 | " | CH$_3$ | " | " | " | " |
| 6 | " | C$_2$H$_5$ | " | " | " | " |
| 7 | " | F | CH$_2$ | " | CHO | " |
| 8 | " | CH$_3$ | " | " | " | " |
| 9 | " | C$_2$H$_5$ | " | " | " | " |
| 10–18 | NH$_2$ | (as in 1–9 ————→ ) | | | | |
| 19–24 | (as in 1–6 ————→ ) | | | | CH$_3$ | (as in 1–6) |
| 25–30 | (as in 10–15————→) | | | | CH$_3$ | (as in 10–15) |
| 31–60 | (as in 1–30 ——————————→ ) | | | | | asp |
| 31–90 | (as in 1–30 ——————————→ ) | | | | | glu—lys |
| 91–120 | (as in 1–30 ——————————→ ) | | | | | glu—asp |
| 121–240 | (as in 1–120) | | | —N—CH$_2$C≡H | (as in 1–120) | |
| 241–360 | (as in 1–120) | | | —N(CH$_3$)— | (as in 1–120) | |
| 361–480 | (as in 1–120) | | | —N(CHO)— | (as in 1–120) | |
| 481–510 | (as in 1–30 ——————————→ ) | | | | | (glu)$_2$ |
| 511–540 | (as in 1–30 ——————————→ ) | | | | | (glu)$_3$ |
| 541–570 | (as in 1–30 ——————————→ ) | | | | | (glu)$_6$ |

-continued

| Compound | R₂ | R₃ | Y | Y' | M | ZZ |
|---|---|---|---|---|---|---|
| 571-660 | (as in 481-570) | | | —N—CH₂C≡CH | | (as in 481-570) |
| 661-750 | (as in 481-570) | | | —N(CH₃)— | | (as in 481-570) |
| 751-840 | (as in 481-570) | | | —N(CHO)— | | (as in 481-570) |

In the column ZZ, "glu" represents glutamyl, "asp" represents aspartyl, and "lys" represents lysyl attached through the α-amino nitrogen. Standard nomenclature is followed for the dimers and oligomers, which are attached as shown in the general formula. Also preferred are compounds in which R₃ is ethenyl or ethynyl and the remainder of the substituents have the combinations of other substituents listed.

Other preferred compounds for use with this aspect of the invention include compounds having the formula

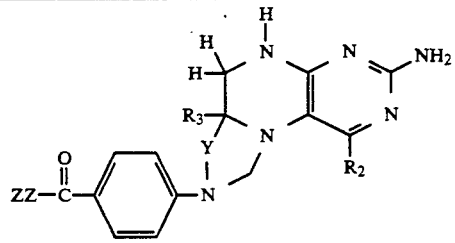

wherein the substituents are as follows.

| Compound | R₂ | R₃ | Y | Y' | ZZ |
|---|---|---|---|---|---|
| 841-846 | (as in 1-6 ⟶ ) | | | | |
| 847-852 | (as in 1-6 ⟶ ) | | | | asp |
| 853-858 | (as in 1-6 ⟶ ) | | | | glu—lys |
| 859-864 | (as in 1-6 ⟶ ) | | | | glu—asp |
| 865-870 | (as in 1-6 ⟶ ) | | | | (glu)₂ |
| 871-876 | (as in 1-6 ⟶ ) | | | | (glu)₃ |
| 877-882 | (as in 1-6 ⟶ ) | | | | (glu)₆ |
| 883-924 | (as in 841-882) | | | —NCH₂C≡CH | (as in 841-882) |
| 925-966 | (as in 841-882) | | | —N(CH₃)— | (as in 841-882) |
| 967-1008 | (as in 841-882) | | | —N(CHO)— | (as in 847-882) |
| 1009-1176 | NH₂ | (as in 841-1008 ⟶ ) | | | |

Also included as preferred compounds are those in which R₃ is ethenyl or ethynyl and the remainder of the substituents have the combinations of the other substituents listed.

The following compounds, having the formula and substituents listed, are especially preferred as inhibitors of thymidylate synthetase. Naturally, these compounds also must of necessity fall within the preferred class of compounds.

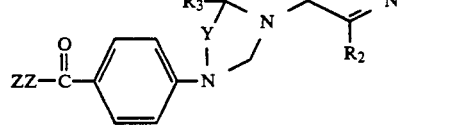

| Compound | R₂ | R₃ | Y | ZZ |
|---|---|---|---|---|
| 1177 | OH | F | CH₂ | glu |
| 1178 | " | CH₃ | " | " |
| 1179 | " | C₂H₅ | " | " |
| 1180 | " | F | CH₂CH₂ | " |
| 1181 | " | CH₃ | " | " |
| 1182 | " | C₂H₅ | " | " |
| 1183-1188 | NH₂ | (as in 1177-1182 ⟶ ) | | |
| 1189-1200 | (as in 1177-1188 ⟶ ) | | | (glu)₂ |
| 1201-1212 | (as in 1177-1188 ⟶ ) | | | (glu)₃ |
| 1213-1224 | (as in 1177-1188 ⟶ ) | | | (glu)₆ |
| 1225-1236 | (as in 1177-1188 ⟶ ) | | | asp |
| 1237-1248 | (as in 1177-1188 ⟶ ) | | | glu—asp |
| 1249-1260 | (as in 1177-1188 ⟶ ) | | | glu—lys |

Also included as especially preferred compounds are those in which R₃ is ethenyl or ethynyl and the remainder of the substituents have the combinations of the other substituents listed.

Furthermore, 6,6-disubstituted tetra- and dihydropteridines can be used in the treatment of other disorders for which tetrahydrobiopterin is a cofactor of the enzyme involved. For example, Parkinson-like symptoms are often induced by antipsychotic drugs, particularly the phenothiazines and butyrophenones and could be counteracted by the activating ability of the 6,6-disubstituted tetrahydropterins. Likewise, compounds of the invention are expected to be useful in the treatment of neurological disorders which have been shown to be associated with low tetrahydrobiopterin levels in the cerebrospinal fluid, such as pre-senile dementia, inherited dystonia, Alzheimer's disease, Shy-Drager Syndrome, Steel-Richardson Syndrome, and Huntington's chorea. Likewise, depression, which is associated with low levels of norepinephrine and/or serotonin, has been successfully treated by administration of one gram tetrahydrobiopterin per day (Levine et al., in *Proceedings of the Second Winter Workshop on Biochemical and Clinical Aspects of Pteridines*, March, 1983, Austria; presented orally and soon to be published by Walter de Gruyter, Berlin). Tetrahydrobiopterin is cofactor for tyrosine and tryptophan hydroxylases, the rate limiting enzymes in the biosynthesis of norepinephrine and serotonin, respectively.

Taking these factors into consideration, suitable compounds for use with the claimed methods of the invention and other compounds which have the other utilities disclosed (especially the utility of replacing biopterin in genetic deficiencies) include compounds having either the tetrahydropteridine ring structure or a dihydropteridine ring structure which can be reduced to the tetrahydro form in vivo. Some of the compounds claimed are useful synthetic intermediates which can be used to synthesize other compounds of the invention. It should be noted that throughout this application and especially in the claims all tautomeric forms are considered to be encompassed by this invention even when only one tautomeric form of the formula of a 6,6-disubstituted compound is given. For example, in the following series of formulae, X-XII are all tautomers of each other. Similar tautomeric forms of compound XV also exist, as do tautomers of the tetrahydropteridines especially when $R_1$ or $R_2$ is hydroxy, in which case the prevalent tautomer is the keto form. Likewise, pharmaceutically acceptable salts (either salts formed by the reaction of bases with acidic functional groups of these compounds or salts formed by the reaction of acids with basic functional groups of these compounds) are specifically contemplated as equivalents of these compounds and especially of the compounds specifically claimed for use with the various methods of use disclosed herein. Accordingly, 6,6-disubstituted compounds of the invention include those having the following formulas:

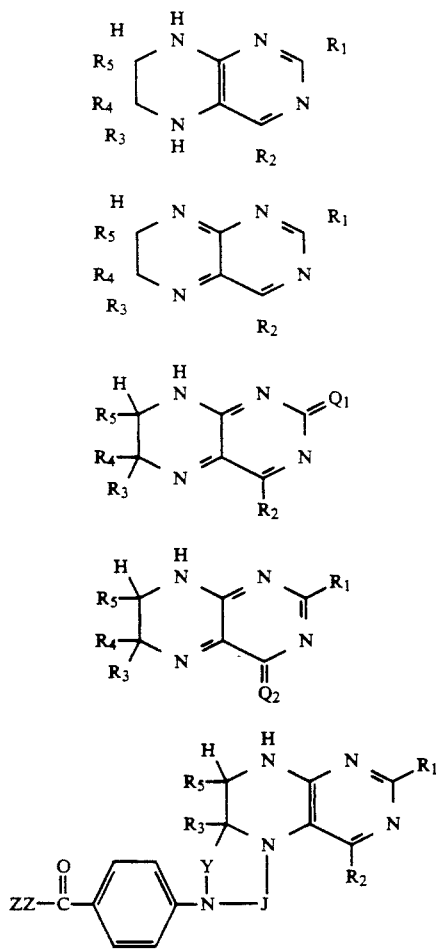
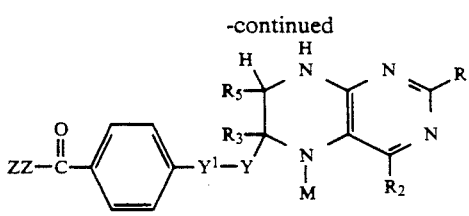
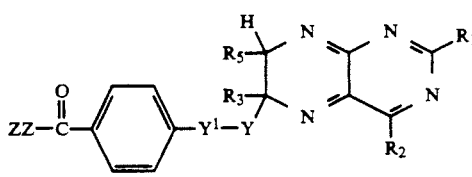
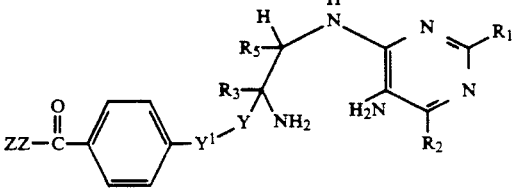
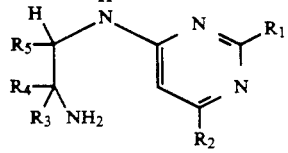
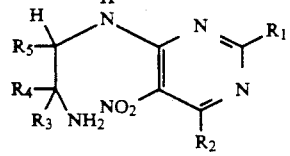
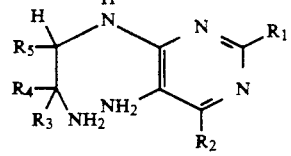
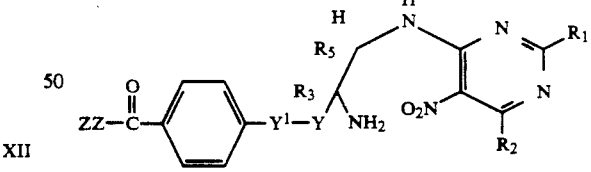

wherein $R_1$ and $R_2$ are the same or different and represent
(1) hydrogen;
(2) hydroxy;
(3) alkoxy of 1 to 4 carbon atoms;
(4) amino of the formula $-NR_6R_7$, wherein $R_6$ and $R_7$ are the same or different and represent
 (a) hydrogen;
 (b) alkyl of 1 to 4 carbon atoms; or
 (c) cycloalkyl of 3 to 6 carbon atoms;
(5) cycloamino selected from the group consisting of
 (a) aziridino,
 (b) azetidino,
 (c) pyrrolidino, (d) piperidino, and
(e) morpholino, wherein said cycloamino is attached to the pyrimidine ring of the formula through a nitrogen of the cycloamino;
(6) alkylthio of 1 to 3 carbons or benzylthio; or
(7) thio with the further provision that not more than one of $R_1$ and $R_2$ is hydrogen;

$R_3$ and $R_4$ are the same or different and represent
(1) alkyl of 1 to 12 carbon atoms;
(2) alkenyl of 2 to 7 carbon atoms;
(3) alkynyl of 2 to 7 carbon atoms;
(4) cycloalkyl, saturated or unsaturated, of 3 to 10 carbon atoms with 3 to 7 atoms in the ring;
(5) bicycloalkyl, saturated or unsaturated, of 6 to 13 carbon atoms with 4 to 7 atoms per ring;
(6) adamantyl;
(7) alkyl of 1 to 12 carbon atoms or alkenyl of 2 to 7 carbon atoms, substituted with 1, 2, 3 or 4 of hydroxy, amino, oxo, thio, phosphate, fluoro, chloro, or bromo;
(8) fluoro, chloro;
(9) amino;
(10) aziridino;
(11) aryl, wherein aryl is phenyl or naphthyl;
(12) arylalkyl of 7 to 13 carbon atoms;
(13) aryl or arylalkyl substituted with 1, 2, or 3 alkyl of 1 to 4 carbon atoms, trifluoromethyl, hydroxy, alkoxy of 1 to 4 carbon atoms, fluoro, chloro, bromo, azido, amino, methylamino, or dimethylamino in the aryl group;
(14) thienyl, thienylmethyl;
(15) furyl, furylmethyl;
(16) tetrahydrofuryl;
(17) pyridyl, pyridylmethyl;
(18) pyridyl substituted with 1, 2, or 3 alkyl of 1 to 4 carbon atoms, amino, hydroxy, chloro, or fluoro;
(19) deuterium;
(20)

wherein $R_{12}$ is a 1- to 22-carbon alkyl or alkenyl group, preferably selected from alkyl and alkenyl groups present in naturally occurring fatty acids and alkyl groups of 1 to 4 carbons; or
(21) carboxyl, and $R_5$ is
(1) hydrogen,
(2) alkyl of 1 to 6 carbon atoms,
(3) cycloalkyl of 1 to 7 carbon atoms,
(4) phenyl, phenylmethyl,
(5) hydroxyl,
(6) alkoxy of 1 to 4 carbon atoms,
(7) amino, or
(8) carboxyl;

Y is methylene or ethylene either of which is unsubstituted or is substituted with 1 or 2 substituents selected from the group consisting of fluoro, chloro, and methyl;
Y' is
(a) —$NR_{10}$—, wherein $R_{10}$ is hydrogen; formyl; formimino; hydroxymethyl; benzyl; or an alkyl, alkenyl, or alkynyl of 1 to 3 carbon atoms,
(b) —$CH_2$—, —$CH(CH_3)$—, —$C(CH_3)_2$—, or —$CH(C_2H_5)$—,
(c) —O—, or
(d) —S—;

ZZ represents the residue of an amino acid or amino acid polymer of the formula

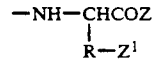

wherein Z represents OH, $C_1$–$C_4$ alkyloxy, or $NH_2$, R represents a divalent alkyl radical of 1 to 5 carbons, and $Z^1$ represents $NH_2$ or $COZ^2$ where $Z^2$ is Z or the residue of an amino acid or amino acid polymer of the formula

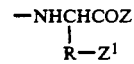

wherein the total number of amino acid residues in ZZ does not exceed 7 and each Z, R, $Z^1$ and $Z^2$ operates independently in defining ZZ;

M is alkyl, alkenyl or alkynyl of 1 to 3 carbon atoms, formyl, formimino, benzyl, hydrogen, or hydroxymethyl; and J is —$CH_2$—, —$CH_2CH_2$—, or =CH—, where the single bond of =CH— is attached to N5;

$Q_1$ and $Q_2$ independently represent O or $NR_6$;

with the provisions that $R_3$ and $R_4$ together may form a 3 to 7 carbon spiro alkyl ring, with carbon 6 of the pteridine ring being the spiro carbon;

$R_4$ and $R_5$ together may form a 5- or 6-membered carbocyclic ring fused to pteridine carbons 6 and 7; if $R_3$ is methyl, $R_4$ is not methyl, cyano, or aminomethyl; and $R_3$ may be deuterium only in a compound having a formula containing an $R_4$ group and if $R_3$ is deuterium, $R_4$ is neither methyl, deuterium, nor phenyl.

In addition to those groups of substituents which have been previously listed as being preferred, $R_4$ is also preferred to be hydroxymethyl or formyl, since compounds having either of these substituents are useful synthetic intermediates for the preparation of other compounds of the invention. Additionally, when a substituted substituent is named (e.g., "alkyl ... substituted with," "aryl or arylalkyl substituted with," etc.) which can itself have several substituents, those which have 1 or 2 substituents (e.g., 2-bromo-4-dimethylaminophenyl) are preferred and those which have one substituent (e.g., 2-hydroxyethyl) are more preferred than more highly substituted substituents.

Furthermore, the substituents at the 6-position that are further removed from the already known 6,6-disubstituted pteridines are preferred in comparison to those compounds which might be considered to be closely related in structure to the known 6,6-disubstituted pteridines, which are believed to be adequately exemplified by 6,6-dimethyltetrahydropterin, 6-carbamoyl-5,6,7,7-tetramethyltetrahydropterin, 6-carboxy-5,6,7,7-tetramethyltetrahydropterin, 6-cyano-6-methyltetrahydropterin, 6-aminomethyl-6-methyltetrahydropterin, 6,7-dimethyltetrahydropterin-6-[$^2$H], 5-acetyl-6-cyano-6-methyltetrahydropterin, and 5-acetyl-6-aminomethyl-6-methyltetrahydropterin. Accordingly, compounds which differ in structure from the listed, known 6,6-disubstituted pterins given in this paragraph by either a functional group listed in this application (e.g., double bond, hydroxyl, keto, amino, etc.) or by at least two methylene groups are preferred (e.g., propyl instead of methyl). Compounds that differ by both a methylene group and a functional group, by at least three methylene groups, or by two functional groups are more preferred, and compounds that differ by three or more functional groups, by a methylene group and two or more functional groups, or by a functional group and two or more methylene groups are most preferred. The difference may occur in one substituent or may be spread over several substituents. The limiting preferences of this paragraph are restricted to limiting the compounds being claimed and are not intended to limit the various methods of use or synthetic techniques being claimed in this application.

Examples of compounds which are believed to be useful as either inhibitors or activators of enzymes for which a pterin acts as a cofactor include those compounds previously discussed for use with the various methods of the invention as well as the following:

2-hydroxy-6,6-di-n-dodecyltetrahydropteridine;
2-n-propoxy-4-amino-6-ethenyl-6-phenylmethyl-7-sec-butyldihydropteridine;
4-cyclopentylamino-6-chloromethyl-6-phenyl-7-methoxytetrahydropteridine;
2-(1-methyl)ethylthio-4-piperidino-6-(1-cyclopentenyl)-6-(2-tetrahydrofuryl)-7-hydroxydihydropteridine;
2,4-diamino-6-cyclopropyl-6-[(4-dimethylaminophenyl)methyl]tetrahydropteridine;
2,4-diamino-6-ethynyl-6-aziridino-7-carboxytetrahydropteridine;
4-morpholino-6-(2-methylbutyl)-6-methyldihydropteridine;
2-pyrrolidino-6-methyl-6-(2-pyridyl)tetrahydropteridine;
2,4-diamino-6-(4-t-butylcyclohexyl)-6-methyl-7-hydroxytetrahydropteridine;
2-amino-4-hydroxy-6-ethyl-6-(2-furylmethyl)tetrahydropteridine;
2-piperidino-4-hydroxy-6-(1-adamantyl)-6-ethyldihydropteridine;
2,4-dihydroxy-6-(2-chloro-4-methylphenyl)-6-aminodihydropteridine;
2-aziridino-4-hydroxy-6-(2-hydroxypropyl)-6-(2-naphthyl)-7-phenylmethyltetrahydropteridine;
2-hydroxy-4-amino-6-deutero-6-ethyltetrahydropteridine;
2,4-diamino-6-amino-6-(3-phosphopropyl)-7-ethyltetrahydropteridine; and
6-deuterotetrahydrobiopterin.

Preferred compounds include those compounds listed as preferred for use with the various methods of the invention. Also preferred are 6-methyl-6-hydroxymethyltetrahydropterin and 6-methyl-6-formyltetrahydropterin, which are useful synthetic intermediates.

Compounds of the invention can be synthesized by any general method of pteridine synthesis now known or discovered in the future. However, as has been previously mentioned, this invention also encompasses a general method of synthesis of pteridines which can be used to synthesize these and other pteridines. This reaction is shown schematically in Scheme I below, where it is illustrated by $R_1=NH_2$ and $R_2=OH$ (i.e., by pterins). Other pteridines can easily be synthesized by the same method using a proper choice of starting pyrimidine, as is fully disclosed in the following paragraphs.

SCHEME I

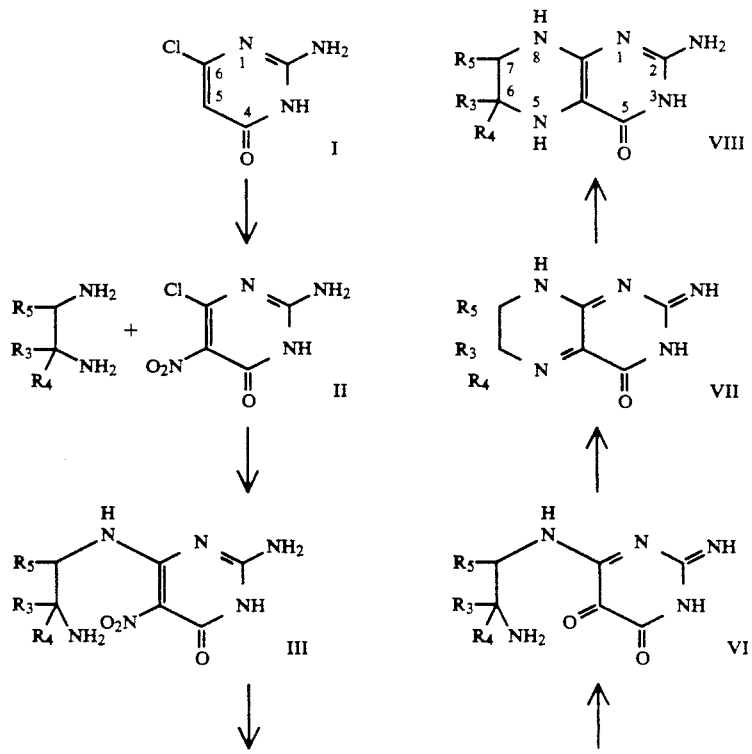

SCHEME I

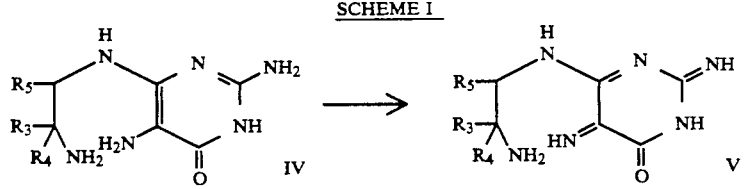

The preferred strategy for the synthesis of the key intermediate compound of formula V involves the nucleophilic displacement of halogen, most conveniently chlorine, from a 6-halo-5-nitropyrimidine by a derivative of 1,2-diaminoethane, preferably one which is unsubstituted or monosubstituted at position 2 and disubstituted at position 1 when a 6,6-disubstituted pteridine derivative is being synthesized. A reaction greatly in favor of condensation of the less hindered amine occurs. The rate constant for aminolysis of a given chloropyrimidine by an N-alkylamine is almost unaffected by increasing the chain length or by γ-branching of the chain. A β-branch has a small and an α-branch a profound slowing effect: one α-branch reduces the rate to ca. 5%, and two such branches to ca. 0.1% of that for the corresponding n-alkylamine. The degree of regiospecific reaction determines the extent to which crude product will be contaminated with the 7,7-disubstituted isomer. Reactions which are greater than 90% directed will occur for the 6,6-disubstituted compounds when the 7-position contains only hydrogen or a small (phenyl or smaller) substituent. This decreases the need for specific protection of the tertiary amine prior to condensation. However, this amino group may be protected by standard techniques if desired, particularly when a tetrasubstituted diamine is being used.

The 5-nitro group is then reduced. A wide variety of methods are available for this reaction, two of the most convenient being discussed below. An alternate route to compound V could be taken by condensation of the diamine with a 4,6-dichloro pyrimidine not containing the nitro group. This requires longer reaction times than when activated by the presence of the nitro group. Hydrolysis of the remaining chloro group can be accomplished with base in ethylene glycol at high temperature in moderate yield. Nitrosation of the 5-position with sodium nitrite and subsequent reduction to the desired amino group by sodium dithionite generally proceeds in high yield.

The objective of the preceding reactions is the making of a pyrimidine which is capable of being oxidized, so that the resulting 5-imine group can be hydrolyzed to a carbonyl. This carbonyl can then enter into a Schiff's base condensation with the tertiary amine of the pyrimidine side-chain, thus closing the pyrazine ring. The requirement that the pyrimidine ring be oxidizable to a quinoid form places some restrictions on the nature of the group(s) on positions 2 and/or 4. The known properties of pyrimidine derivatives indicate that three or more electron donating substituents are required to make the pyrimidine susceptible to mild oxidants. This condition is fulfilled by the choice of the starting pyrimidine such that one or two such groups be located at positions 2 and/or 4, addition of two amino groups at positions 5 and 6, as above, making the final necessary complement. Examples of patterns of particular biological interest are 2-amino-4-hydroxy (precursor to pterins), 2,4-dihydroxy (precursor to lumazines), and 2,4-diamino (common to many anti-folate drugs). Pyrimidines with many combinations of the above electron releasing groups at positions 2 and/or 4 with chlorine at position 6 are commercially available. In particular, 2-amino-6-chloro-4-hydroxy-, 2,4-dihydroxy-6-chloro-, and 2,4-diamino-6-chloropyrimidine are all commercially available (Aldrich Chemical Co., Milwaukee, Wis., or K and K Labs, Plainview, N.Y.). Furthermore, appropriate methods for the nitration of each of these compounds are known as will be exemplified later.

A wide variety of methods are known for the synthesis of diamines. One which is particularly appropriate for the making of vicinal diamines which are precursors to 6,6-disubstituted pteridines in which $R_5$ is hydrogen is that of Freifelder and Hasbrouck, *J. Amer. Chem. Soc.*, 82, 696–698 (1960), which is herein incorporated by reference. In general, this method allows ketones and aldehydes of the formula $R_3COR_4$ to be converted into α-aminonitriles of the formula $R_3R_4C(NH_2)CN$ which are then reduced to 1,2-diamines of the formula $R_3R_4C(NH_2)CH_2NH_2$. The following Table shows a series of commercially available ketones and the resulting diamines that are converted into the pyrazine ring of the pteridine ring system by the synthetic method of this invention.

TABLE

| Commercially available ketone | Diamine produced |
|---|---|
| ≡—⟨—C(=O)— | ≡—⟨—C(N)(N) |
| [thiophene]-C(=O)— | [thiophene]-C(N)(N) |
| $CH_3O$-[phenyl]-CH$_2$-C(=O)- | $CH_3O$-[phenyl]-CH$_2$-C(N)(N) |
| F-CH$_2$-C(=O)- | F-CH$_2$-C(N)(N) |
| [cyclobutyl]-C(=O)- | [cyclobutyl]-C(N)(N) |

An even more general synthesis of diamines is disclosed in Beckham et al., *Chem. Reviews*, 48, 319–383 (1951), pages 369–378 of which are herein incorporated by reference, and in Berger et al., *J. Prakt. Chem.*, 320 433–451 (1978), which is herein incorporated by reference. This method converts alkenes of the formula R$_3$R$_4$C=CHR$_5$ into diamines of the formula CR$_3$R$_4$NH$_2$CHR$_5$NH$_2$ by a series of reactions involving nitrosyl chloride addition across the double bond followed by displacement of the chlorine atom by ammonia and reduction of the nitroso group to an amine. This second method is particularly useful for producing the fused-ring and spiro compounds claimed. For example, methylenecycloalkanes produce diamines that are converted into spiro compounds, and cycloalkenes produce diamines that are converted into fused-ring compounds. Other substituents than alkyl can likewise be introduced by a careful selection of starting alkenes. For example, the following Table shows a series of commercially available alkenes and the resulting diamines that are converted into the pyrazine ring of the pteridine ring system by the synthetic method of this invention.

It should be noted that the last diamine contains a double bond that can be converted into a biopterin like 1,2-dihydroxypropyl side chain by epoxidation and hydrolysis. Similar conversions of other side chains allow the remaining claimed side chains to be readily synthesized as is well understood to one of ordinary skill in the art of organic synthesis. For example, thio groups at positions R$_1$ and R$_2$ are best prepared using a benzylthio precursor in order to prevent dimerization during the oxidation steps of the ring closure reaction. The benzyl group is removed, if desired, by hydrogenolysis. Similarly, bromine or chlorine as substituents on alkyl groups at positions R$_3$ and R$_4$ are best added by halogenation or hydrohalogenation of a double bond in an alkenyl group since amino-containing alkyl bromides or chlorides would tend to self-condense during the initial ring formation steps. Thio groups on R$_3$ and R$_4$ can be protected during synthesis with groups such as p-methoxybenzyl, benzyl, t-butyl or triphenylmethyl; oxo can be protected in groups such as cyclic dioxolane, 1,3-oxathiolane, cyclic dithioketal or ketal; and amino can be protected with groups such as benzyloxycarbonyl, t-butoxycarbonyl, 2-(4-biphenyl)-prop-2-yl-oxycarbonyl, 2-nitrophenylsulfenyl, 9-fluorenylmethyloxycarbonyl, or acetal.

Furthermore, the various side chains can be synthesized separately by convetional methods of organic synthesis followed by attachment to the pteridine ring through a reactive R$_3$, R$_4$, or R$_5$ group. For example, the folate analogs (all of which have a p-aminobenzoic acid-containing side chain) can be prepared by separately synthesizing the p-aminobenzoic acid-containing group and reacting the free amino group of the benzoic acid moiety with an $R_4$ group of the formula CHO— or CHOCH$_2$— (or a suitable derivative thereof having one or more hydrogens replaced as previously defined) followed by reduction of the resulting Schiff's base.

According to one preferred aspect of this invention, which is included as an exemplary general synthesis and is not intended to be limiting, a 6,6-disubstituted quinoid dihydropteridine is synthesized first by reaction of a vicinal diamine and 2-amino-6-halogeno-4-hydroxy-5-nitropyrimidine. Conveniently the halogen may be chlorine. High pressure liquid chromatography (HPLC) indicates that the product isolated from this and subsequent reactions contains little ultraviolet absorbing or electrochemically active impurities, if both the diamine and the pyrimidine are initially pure.

The purity of the diamine with respect to other potentially competing amines can be ascertained by the reverse-phase HPLC method of Lindroth and Mopper, *Anal. Chem.*, 51, 1667–1674 (1979). Commercial 2-amino-6-chloro-4-hydroxypyrimidine is, however, frequently contaminated with other pyrimidines. If the initial contaminants are not largely eliminated from this starting material, significant losses are incurred in their removal later in the process. To that end, 2-amino-6-chloro-4-hydroxypyrimidine may be obtained in nearly pure form by recrystallization from 1N HCl. Recovery from this solvent, however, is somewhat limited by hydrolysis to 2-amino-4,6-dihydroxypyrimidine at elevated temperature. An effective compromise between purity and yield results from the addition of a few percent of a low boiling point, water miscible solvent, such as methanol, and limiting the time that material is exposed to reflux temperature.

The known methods for the nitration of 2-amino-6-chloro-4-hydroxy-pyrimidine all have in common the use of a large excess of nitric acid. Analysis of this reaction by HPLC shows that only a 10–20% molar excess of nitric acid is necessary, and that increasing the amount of this reagent further only promotes the nitration of any impurities which may be present. Also, the published methods all call for the precipitation of product by pouring the reaction mixture onto crushed ice. One aspect of this invention is an improvement in the method of recovering the 2-amino-6-chloro-4-hydroxy-5-nitropyrimidine whereby, upon completion of the nitration, the reaction mixture is poured slowly into a di-$C_1$-$C_4$-alkyl ether, with stirring, and kept cold on ice. The desired nitrated pyrimidine precipitates and recovery is further improved by storage of this solution in the cold. The major advantage of this method over the use of ice is the differential precipitation of the 2-amino-6-chloro-4-hydroxy-5-nitropyrimidine, leaving most of the impurities left from incomplete purification of the 2-amino-6-chloro-4-hydroxypyrimidine still in solution. Ethyl ether may be used, but t-butyl methyl ether is preferred for the purity of product it precipitates and for its greater miscibility with sulfuric acid.

The reaction of 2-amino-6-chloro-4-hydroxy-5-nitropyrimidine with a substituted 1,2-diaminoethane can be conveniently carried out by refluxing in an absolute alcohol with a boiling point in the range 60°–120° C. The advantages of ethanol, which is preferred, are as follows: (1) 2-amino-4,6-dihydroxy-5-nitropyrimidine, the main impurity (approximately 1–4 percent) of the nitration of purified 2-amino-6-chloro-4-hydroxypyrimidine, is relatively insoluble in hot ethanol and may be removed by filtration prior to addition of the amine; (2) the above chloronitropyrimidine is at least somewhat soluble in hot ethanol; (3) the temperature of refluxing ethanol is such that most reactions are complete within a few hours; and (4) the products of reaction with most substituted 1,2-diaminoethanes are insoluble, especially in cold ethanol. The use of absolute ethanol minimizes hydrolysis of the above chloronitropyrimidine, although further drying of most commercial grades of absolute ethanol is not required. The substituted 1,2-diaminoethane is best added as the free base. If the free base is not obtainable or its use impractical, a base unreactive toward displacement of the pyrimidine halogen, for example triethylamine, can be added to the reaction as a halide scavenger. If desired, such a base may be added in other reactions in order to promote completion of the reaction. The optimal amount of base can be determined by monitoring the progress of the reaction by HPLC. A slight excess of the diamine, approximately 5–10 percent, can be used in order to force complete consumption of the 2-amino-6-chloro-4-hydroxy-5-nitropyrimidine. Large excesses often decrease the rate of reaction and eventual yield. Yields are, in general, greater than 90 percent based upon the limiting reagent. If a lower yield is obtained, the purity of the starting 2-amino-6-chloro-4-hydroxy-5-nitropyrimidine should first be checked.

Catalytic hydrogenation of a pyrimidine 5-nitro group, which often proceeds in high yield, gives only moderate to poor yields in the reduction of the product of the condensation of a substituted 1,2-diaminoethane with the 2-amino-6-chloro-4-hydroxy-5-nitropyrimidine. The absence of ultraviolet absorbing by-products is an indication that some cleavage of the pyrimidine ring may be occurring. Yields from catalytic reductions are increased if palladium is used instead of platinum, rhodium, ruthenium or Raney nickel. Further yields obtained using unsupported PdO or 5% Pd on barium sulfate are 10–15% higher than with palladium on charcoal.

Compared to catalytic hydrogenation, higher yields usually result from the use of dithionite as reducing agent. A second advantage of dithionite is its selective reduction of the nitro group in the presence of other groups which may be sensitive to catalytic hydrogenation. A modification of the procedure of Nair et al.., *J. Org. Chem.*, 140, 1745–1748 (1975), is especially effective. The cited method calls for the gradual addition of water to a heated slurry of nitropyrimidine and sodium dithionite in dimethyl formamide. The modification changes the order of addition of reagents. A solution of the product of the condensation of a substituted 1,2-diaminoethane with 2-amino-6-chloro-4-hydroxy-5-nitro-pyrimidine, in an approximately 1:1 mix of water and dimethylformamide is heated to between 50° and 70° C. It is desirable that this solution be as concentrated as possible, a condition that can be aided in some cases by the addition of up to one equivalent of a base, such as sodium hydroxide. With constant stirring and flushing of the reaction vessel with inert gas, fresh solid sodium dithionite is added in aliquots until analysis by HPLC indicates completion of the reduction. The advantage of this modification is the use of minimum amount of dithionite in order to achieve complete conversion of the nitro to an amino group.

The removal of the bulk of the sulfur-containing inorganics resulting from the use of dithionite aids in the subsequent extraction of the desired product 6-(2-aminoethylamino)-2,5-diamino-4-hydroxypyrimidine, substituted in the ethyl moiety into a minimal volume of solvent. Also, if the bisulfite product of dithionite is not removed, it will consume oxidant (see below). The removal can be accomplished, in part by addition of barium chloride in aliquots until no further precipitate is formed. After removal of the precipitate, either by centrifugation or filtration under inert atmosphere, the solution is acidified with a strong acid such as HCl and rotary evaporated or lyophilized to remove water and/or dimethylformamide. This evaporation, which also serves to remove sulfur dioxide, is best accomplished under reduced pressure such that the compound can be maintained at room temperature; otherwise premature oxidation by air may occur.

The cyclization of the above substituted 6-(2-aminoethylamino)-2,5-diamino-4-hydroxypyrimidine requires oxidation followed by hydrolysis of the 5-imine group in the resulting quinoid pyrimidine. This hydrolysis is promoted by an acidic environment. Hydrolysis replaces the 5-imine with a carbonyl group, forming a derivative of quinoid divicine. A Schiff's base condensation can then take place between this carbonyl group and the terminal amino group of the substituted 2-aminoethylamino side chain. This reaction is promoted by a neutral environment. Thus, although it is possible to cyclize V in a single environment over a broad pH range, a two-step process, with pH optimization at each, promotes higher yield. A second factor affecting recovery is the instability of the above quinoid divicine derivative in primarily aqueous media at all pH's. For example, although 6,6-dimethyl quinoid dihydropterin may be obtained in modest yield by oxidative cyclization in water, a primarily nonaqueous solvent containing sufficient water to allow hydrolysis of the 5-imine group is generally more suitable. However, the amount of water present may be adjusted to optimize the yield. For example, hydrophobic substituents in the 6-position are expected to retard hydrolysis, and a higher concentration of water is likely to be needed. Ability to dissolve the substituted 6-(2-aminoethylamino)-2,5-diamino-4-hydroxypyrimidine, good volatility, and lack of reaction with subsequent oxidant are desirable properties of the solvent. A low molecular weight alcohol such as methanol can often be used. In some instances the trace water in analytical grades of methanol are sufficient for rapid hydrolysis of the oxidized pyrimidine. Methanol is also a convenient medium for catalytic reduction of the nitro group should this route be chosen. The solution of reduced material, after thorough removal of catalyst, can be used directly for oxidative cyclization.

A halogen, conveniently bromine, may be used as oxidant. Iodine is equally effective. In the acidic, nonaqueous solvent preferred for the oxidation an excess of halogen of approximately 40 percent is generally required. The optimal amount of oxidant is best determined by monitoring the disappearance of the substituted 6-(2-aminoethylamino)-2,5-diamino-4-hydroxypyrimidine using a rapidly eluting HPLC system. The completion of the ensuing hydrolysis may also be monitored by HPLC. An indication of either incomplete oxidation and/or hydrolysis is the contamination of the final 6,6-disubstituted tetrahydropterin with substituted 6-(2-aminoethylamino)-2,5-diamino-4-hydroxypyrimidine. A rate of hydrolysis that is favorable in comparison to the rate of destruction of the quinoid pyrimidine intermediates can be obtained by optimizing the acidity of the reaction medium. In those cases requiring only minimal water, hydrolysis may be accelerated by including acid, for example trifluoroacetic, in addition to that which is generated by the oxidation itself. An amount greater than 2 moles per mole of pyrimidine is usually unnecessary. When higher water concentrations are used, control of reaction acidity by addition of a base, such as sodium hydroxide, to between pH 0 and 5 and preferably between pH 1 and 3 is desirable. Other oxidants which are believed to be useful include chlorine (particularly in the form of hypochlorite), ferricyanide, bromate, iodate, periodate, and dichlorophenolindophenol (DCIP).

Upon completion of the hydrolysis of the oxidized substituted 6-(2-aminoethylamino)-2,5-diamino-4-hydroxypyrimidine, the reaction mixture is neutralized. Reactions performed in solvents containing minimal water are preferably neutralized with a nonaqueous base (as an example sodium methoxide dissolved in methanol; triethylamine is nearly as effective). In reactions containing higher amounts of water, an aqueous base may be used. The pH of a 10-fold dilution of a sample of the reaction into water is titrated to between about pH 4 and 10, optimally between pH 6.5 and 7.5. The 6,6-disubstituted quinoid dihydropterin nucleus has a pKa for the transition from neutral to monocation of near pH 5.1. Between pH 6.5 and 7.5 the cyclized product is the neutral molecule (not accounting for any charges that may be carried in the side chains) and is generally both maximally stable and insoluble. A rapid rate of cyclization is also promoted by near neutral conditions. Product may also be collected by evaporation of solvent but will contain the inorganic salts. Quinoid dihydropterins containing hydrophobic substituents are generally sufficiently insoluble in water that they can be slurried in water and filtered or centrifuged to remove these salts. A subsequent wash with ethyl ether will remove any excess unreacted halogen. Vacuum-dried quinoid dihydropterins may be stored for several months if kept desiccated at −80° C.

When a 6,6-disubstituted tetrahydropterin is desired, several options are available for reduction of the above quinoid dihydropterin. A catalyst such as palladium or platinum, supported or unsupported, may be added to the neutralized alcoholic solution obtained above and the dihydropterin hydrogenated. Alternatively, a fresh aqueous solution of a slight excess of sodium dithionite, preferable deoxygenated with inert gas, may be added to the dihydropterin following evaporation of solvent. The reaction proceeds rapidly and in high yield but has the disadvantage of introducing further salts. Conveniently, an aqueous solution of a thiol that is soluble in both water and ether, for example mercaptoethanol, may be added to the dihydropterin following removal of solvent. The bulk of all of the organic solvent is best removed, as reduction by thiols is usually inefficient in solvents that are not primarily aqueous. As reduction occurs, the generally sparingly-water-soluble quinoid dihydropterin is converted into a more soluble tetrahydropterin. The reaction can be monitored by HPLC or spectrophotometrically. The near elimination of the yellow coloration due mainly to quinoid dihydropterin also provides a visual indication of completion of the reaction. The addition of thiol in a minimal volume required to dissolve the reduced pteridine will expedite the subsequent evaporation of solvent. In order to minimize exposure of quinoid dihydropterin to aqueous conditions, an excess of concentrated thiol may be used.

These quantities vary with the thiol; an approximately 1.5 to 4-fold excess of 1M 2-mercaptoethanol provides a rapid reaction at room temperature. More hydrophobic compounds may require larger volumes of somewhat more dilute thiol in order to solubilize the tetrahydro product.

A strong mineral acid, such as hydrochloric, is added to the above solution of 6,6-disubstituted tetrahydropterin, and solvent is remove without exposure to elevated temperature, for example by rotary evaporation at reduced pressure or by lyophilization. Optimal stability during storage usually results when the quantity of mineral acid is adjusted so that the pteridine ring of the final 6,6-disubstituted tetrahydropterin is mono- to dicationic. A possible exception to this general rule is compounds with acid labile groups in the side chains, for example 6,6-disubstituted analogs of tetrahydrofolic acid, in which case a different salt form may be optimal as is well-known to those skilled in the art. The excess thiol and the disulfide produced by oxidation of the thiol may then be washed from the dried tetrahydropterin salt. The purity of many tetrahydropterins, including some which are 6,6-disubstituted, is often improved by solution of their hydrohalide salts in methanol or absolute ethanol, followed by precipitation using several volumes of ethyl ether.

The individual steps of this reaction scheme may be optimized for the synthesis of particular compounds, as is well-understood by those skilled in the art of organic synthesis. For example, one equivalent of a hydrogen halide scavenger, preferably triethylamine, is believed to be needed to allow complete condensation of any highly hydrophobic diamine with the starting halopyrimidine. Likewise, solvent, pH, and temperature may be optimized in order to increase yields. Further guidance can be obtained by reference to the examples which follow, which show the types of modification that have been conducted in order to optimize the syntheses of 6,6-dimethyl- and 6-methyl-6-phenyltetrahydropterins to the present degree.

In addition to the synthesis of the compounds previously mentioned which can be used for carrying out the treatments involving hydroxylase and thymidylate enzymes that are a part of this invention, this synthetic method also includes synthesis of other pteridine compounds. In its most general form, this method encompasses synthesizing the 6,6-disubstituted pteridine ring system itself from a monocyclic precursor and is not limited to synthesizing compounds having the specific side chains or functional groups shown in this application.

Additional conventional steps, such as oxidation, alkylation, and other modifications of the side groups obtained in the process given in the preceding paragraphs are necessary to reach some pteridines of different structures, as is well-understood by those skilled in the art of organic chemical synthesis. For example, the M group or methylene bridge of a folate analog can be added by known methods to the basic substituted pterine structure made by the general synthesis of this invention. Likewise deuterium can be introduced at the 6-position of a 6-mono-substituted pteridine, for example prepared according to a general procedure described in Pfleiderer, *Angewandte Chemie, Int. Ed.*, 3, 114-132 (1964), by the method of Archer et al., supra.

When compounds of the invention are used as aromatic amino acid hydroxylase activators, they are administered to a human or animal in need of such activation in an amount sufficient to increase the activity of the enzyme. This amount will vary depending on the severity of the disorder being treated. Adjustment of dosage levels to optimal levels is common practice in the pharmaceutical arts and with humans is commonly done by the physician doing the administering. Administration may be by any method which allows the active compound to reach the bloodstream. Typical methods include intravenous injection and oral administration (optionally in enteric form). Oral administration is preferred. The compounds of the invention can be prepared in pharmaceutical preparations containing the compounds themselves with a pharmaceutically acceptable carrier. The pharmaceutically acceptable carrier may be a solid or liquid. Examples of liquid carriers include water and aqueous solutions of non-toxic salts, such as sterile physiological solutions of saline, or aqueous solutions containing organic solvents, such as ethanol, used to increase the amount of pteridine in solution. Also suitable are emulsions, such as oil-in-water emulsions. Solid carriers include both nutritive carriers, such as sucrose or gelatin, and non-nutritive carriers, such as cellulose or talc. Other substances may also be presented, such as ascorbic acid, which may be added to maintain the tetrahydropteridine in the reduced form, or a substrate of the enzyme being activated such as tryptophan or tyrosine, or flavorings. When prepared as a pharmaceutical composition, preparation in a unit dosage form (see below) is preferred.

Amounts of pteridines useful as enzyme activators can be determined by simple experimentation as is well-understood by those skilled in the pharmaceutical arts. Amounts in the range from 0.1-100 mg/kg body weight are preferred as initial dosages, which may be adjusted as necessary. Especially preferred are amounts in the range of 1-10 mg/kg body weight since compounds of the invention, because of their greater stability and high lipophilicity, are generally more active in vivo than the 6-monosubstituted pteridines previously used and described in the section of this application dealing with the background of the invention. Administration 3 or 4 times daily at equal intervals is preferred. A total daily dosage of 0.5-50 mg/kg is preferred.

Similar methods of administration, carriers, etc. may be used when the compound being administered is an inhibitor of thymidylate synthetase. However, the preferred initial dosage range for internal administration is 0.01-10 mg/kg with 0.1-1 mg/kg being especially preferred. A total daily dosage of 0.05-5 mg/kg is preferred. Additionally, a thymidylate synthetase inhibitor may be used topically, for example as a wound dressing to prevent or treat a bacterial, fungal, or protozoal infections. In such cases, administration in a cream or ointment is preferred, although solutions may be used to wash the afflicted body part, if desired. Topical administration in a carrier at a concentration of from 0.1 to 2% by weight of the carrier is preferred.

Although treatment of humans is the preferred subject of this invention, other higher animals may likewise be treated, particularly with thymidylate synthetase inhibitors. Preferred are mammals and birds, with cattle, horses, dogs, cats, sheep, goats, chickens, hogs, and turkeys being most preferred.

The above disclosure generally describes the present invention. A more complete understanding can be obtained by reference to the following specific examples which are provided herein for purposes of illustration only and are not intended to be limiting unless otherwise specified.

Example I: Synthesis and Properties of 6,6-dimethyltetrahydropterin

In this example Roman numerals followed by (a) refer to the structures shown in Scheme I in which $R_3$ and $R_4$ are methyl groups and $R_5$ is hydrogen.

2-Amino-6-chloro-4-hydroxy-5-nitropyrimidine (II)

2-Amino-6-chloro-4-hydroxypyrimidine (I) was recrystallized once from 1N HCl/methanol, 95:5, with minimal exposure to reflux temperature. The purity of this material was examined at various wavelengths upon elution from a Partisil SCX column (25×0.46 cm) with 10 mM ammonium hydroxide made to pH 3.3 with formic acid. In this buffer, pure material had the following UV absorbing properties:

($\lambda$max224,284; $\lambda$min246 nm)$\epsilon^{284}/\epsilon_{246}$=10.0 and $\epsilon^{284}/\epsilon_{320}$>300.

After 12 hrs in vacuo over $P_2O_5$, 1.64 g (I) (10 mmole of monohydrate) was dissolved in 10 ml $H_2SO_4$ precooled on ice to prevent hydrolysis. Nitric acid, 90%, 0.8 g (11.4 mmole) was added dropwise with stirring to the cold mixture so that its temperature remained below 6° C. It was then allowed to warm to 25° and was stirred for 3 hrs. HPLC analysis on the above system indicated the complete disappearance of starting material. The product was dropped slowly into 100 ml cold t-butyl methyl ether with stirring on ice so that the temperature was maintained below 10° C.; the resulting suspension was kept at −15° C. overnight. The precipitate was collected by filtration and washed with ethyl ether until the filtrate contained no acid (approximately 150 ml) as determined by test with $BaCl_2$. After vacuum-drying over $P_2O_5$, this material weighed 1.94 g, and analysis by HPLC indicated a 3% contamination with 2-amino-4,6-dihydroxy-5-nitropyrimidine. No other significant peaks were observed during monitoring at 254, 282, and 330 nm. A broad $^1$H-NMR peak between 8 and 10 ppm in DMSO-$D_6$ integrated in comparison with an internal standard indicated the probable inclusion of 1 mole of water per mole of pyrimidine despite the primarily nonaqueous method of product recovery. When the weight of the hydrolyzed impurity is subtracted, the above weight indicates a yield of 90% of monohydrate.

2-Amino-6-(2-amino-2-methylpropylamino)-4-hydroxy-5-nitropyrimidine monohydrochloride (IIIa)

2-Amino-6-chloro-4-hydroxy-5-nitropyrimidine, 1.94 g, was finely powdered and dissolved in approximately 200 ml boiling absolute ethanol and filtered while hot to remove the insoluble 2-amino-4,6-dihydroxy-5-nitropyrimidine (sole contaminant), leaving a solution containing 9.0 mmoles of (IIa). This was taken again to reflux and 0.88 g (20 mmoles) 1,2-diamino-2-methylpropane (99% pure) added all at once with stirring. The progress of the reaction was monitored on Partisil SCX (25×0.46 cm) eluted with 0.1M ammonium hydroxide made to pH 3.3 with formic acid/methanol, 9:1, by absorbance at 254 and 330 nm. After 2 hrs stirring at reflux, greater than 99% of (IIa) had been consumed and the majority of product had fallen out of solution. After being kept at −15° C. overnight in order to complete this precipitation, the reaction, filtered, washed with a few ml cold absolute ethanol and 40 ml ether, and vacuum dried over $P_2O_5$, gave 2.43 g of the monohydrochloride salt (97% yield): UV (0.1N HCl) $\lambda$max 331 nm, 285-290 nm sh, 233 nm sh; $^1$H-NMR (DMSO-$D_6$) δ1.13 (6H, s, C(CH$_3$)$_2$), δ3.50 (2H, d, J=5 Hz, —N—CH$_2$ (singlet if $D_2O$ added). Greater than 99% of the UV$_{330}$ and 98% of the UV$_{254}$ absorbance in a chromatogram of this material resides in a single well-shaped peak. No evidence for the presence of any 2-amino-6-(2-amino-1,1-dimethylethylamino)-4-hydroxy-5-nitropyrimidine can be seen by either HPLC or NMR.

6-(2-Amino-2-methylpropylamino)-2,5-diamino-4-hydroxypyrimidine dihydrochloride (IVa)

A suspension of 2.23 g (IIIa) (8.0 mmole) in 80 ml dimethyl formamide and 80 ml water plus 0.16 g of NaOH (4.0 mmole) was thoroughly argonated and heated to 60° C. While stirring, aliquots of fresh sodium dithionite, about 6 mmole each, were added under a constant stream of argon. Addition of reductant was continued until analysis on Partisil SCX (25×0.46 cm) eluted with 1.0M ammonium hydroxide plus formic acid to pH 3.3/methanol/1 mM Na$_2$EDTA, 1:1:3, indicated only 1% of (IIIa) remaining; at this time the solution was nearly clear. Approximately 5.6 g Na$_2$S$_2$O$_4$ (32 mmole) had been used. (The required amount was found to vary between 3.5 and 6 moles per mole of (IIIa), depending on the state of the reagent and the timing of the addition.) Aside from a few minor peaks at the solvent front, due primarily to the dithionite, HPLC showed only a single impurity eluting as a rear shoulder of the main product. The majority of this by-product, which absorbs at 262 nm in 0.1N HCl, could be removed by centrifugation after cooling the reaction mixture on ice. Aliquots of 1M barium chloride were added to the above supernate and centrifuged, until no further precipitate formed. A total of about 14 ml of 1M barium chloride (approximately 40 to 50 mole % of the dithionite added) was needed.

The final barium precipitate was resuspended in a few ml of cold argonated water and centrifuged. The resulting supernate together with the initial main supernate and 2.8 ml concentrated HCl were rotary evaporated to near dryness at 25° C.

Product was partially separated from the remaining salts by extraction into spectrophtometric grade methanol (~350 ml) until less than 1% remained in the solids. The solution was then quickly argonated to prevent oxidation of (IVa). Based upon an assumed extinction coefficient of 16,000 at $\lambda$max 269 nm in 0.1N HCl, and on the purity of the product determined chromatographically with UV$_{269}$ detection (90%), an approximate yield of 85% from (IIIa) was estimated: $^1$H-NMR (relative to TSP) (D$_2$O/DCl) δ1.38 (6H, s, C(CH$_3$)$_2$, δ3.63 (2H, s, —N—CH$_2$—).

Compound (IVa) was also obtained by catalytic reduction of (IIIa) (1 g) over an equal weight of 5% Pd on BaSO$_4$ in methanol (50 ml), stirred 14 hrs under 45 psi H$_2$ at room temperature. A product free of UV absorbing impurities but in somewhat reduced yield (60–65% as estimated above) was thus obtained. Care was taken to completely remove catalyst, which efficiently promotes air oxidation. The methanolic solution of (IVa) from either method may be concentrated and product precipitated with 5–10 volumes of ether to give the dihydrochloride salt plus some NaCl.

2-Amino-6,6-dimethyl-4-hydroxyquinoiddihydropteridine

A solution of (IVa) (approximately 6.8 mmole obtained by dithionite reduction of 8.0 mmoles of (IIIa) in spectrophotometric grade methanol was concentrated by rotary evaporation to a volume of about 150 ml (approximately 45 mM) and 1 ml trifluoroacetic acid added. To this mixture, at 25° C., was added 1.31 g bromine (8.2 mmole) all at once with stirring. The oxidation was monitored by the same chromatographic system as used in the synthesis of (IVa). A further 0.32 g bromine (2.0 mmole) was found necessary to eliminate the chromatographic peak due to (IVa). Insufficient oxidant may also be determined by the gradual appearance of a purple coloration, whereas a correctly titrated reaction is yellow. Addition of the final portion of bromine was made within 5 minutes of the first. After a further 5 minutes all of the oxidized (IVa) had been hydrolyzed by trace water in the methanol to the 6N-(2-amino-2-methylpropyl) derivative of quinoid divicine (VIa), and therefore the solution was taken, over a period of 10 min, to between pH 6.6 and 7.0 (as determined by 10-fold dilution of an aliquot into water) with 1M sodium methoxide in methanol. Upon neutralization, (VIa) immediately condenses forming (VIIa) which may begin to form a bright yellow precipitate. Quinoid-6,6-dimethyldihydropterin may be collected by concentration of the neutralized solution with subsequent cooling, or may be reduced to 6,6-dimethyltetrahydropterin.

6,6-Dimethyltetrahydropterin (VIIIa)

The above methanolic suspension of VIIa (the result of dithionite reduction of 8.0 mmole (IIIa) and subsequent oxidative cyclization) was rotary evaporated to dryness at ambient temperature. The yellow quinoid was reduced and thus dissolved at room temperature in a minimal volume (50 ml) 1.0M 2-mercaptoethanol in water. The light yellow solution was rotary evaporated together with 5 ml concentrated HCl to an oily suspension, from which the (VIIa.2HX) was extracted with several washes of methanol totalling 60 ml, leaving behind some salts.

This solution was concentrated to 25 ml, and 6–8 volumes of ether were added. The precipitate formed was collected by centrifugation, resuspended in 150 ml fresh ether, recentrifuged, and the precipitate dried under vacuum. The resulting light yellow powder weighed 1.98 g and contained about 29% sodium halide, primarily chloride. HPLC analysis using the same conditions as in the synthesis of (IVa) indicated that greater than 98% of the absorbance area at either 254 nm or 266 nm was located in a single peak, the major impurity ($\frac{1}{2}$%) having a retention volume identical to the by-product introduced by dithionite reduction of (IIIa). A UV response in the solvent front at this point occasionally resulted from incomplete removal of oxidized 2-mercaptoethanol during the above ether precipitation. No other electrochemically active (0.4 V vs. Ag/AgCl on glassy carbon) compounds were detected. The yield of (VIIIa), determined spectrally in 0.1N HCl using an extinction coefficient of 14,700$M^{-1}$cm$^{-1}$, was found to be 5.24 mmole (65% from (IIIa), 57% from (Ia)). Completely colorless (VIIIa.2HCl), of even higher purity may be obtained with good recovery by application of the method used by Weber et al., *Helv. Chim. Acta*, 57 1485–1492 (1974) for the crystallization of 6-methyl-5,6,7,8-tetrahydropterin. This Weber et al. article is herein incorporated by reference.

Chemical Properties of 6,6-Dimethyltetrahydropterin: UV

The UV absorbing properties of 6,6-Me$_2$PH$_4$ are summarized in Table I. The concentration of a stock solution of 6,6-Me$_2$PH$_4$ was established by titration with 2,6-dichlorophenol-indophenol at pH 5.5, with ascorbic acid as standard, immediately before determination of the extinction coefficient at pH 1.0 at 265 nm. This value was used to determine concentrations of all subsequent solutions including those used for the evaluation of extinction coefficients at other pH's.

TABLE I

| UV Absorbing Properties of 6,6-Dimethyltetrahydropterin | | | |
|---|---|---|---|
| pH | Buffer | λmax | Em(M$^{-1}$cm$^{-1}$) |
| 7.4 | 0.039 M sodium potassium phosphate (NBS) | 220 303 (340) | 19,700 9,700 (700) |
| 3.3 | 0.01 M ammonium formate | 218 266.5 | 27,200 12,800 |
| 1.0 | 0.1 N HCl | 265 216 | 14,700 16,200 |
| 0 | 1.0 N HCl or 5% H$_2$SO$_4$ | 265 no other peak above 200 nm | 16,500 |

NMR: The $^1$NMR data, acquired at 60 MHz, are: in (CD$_3$)$_2$SO+1 NaOD to 6,6-Me$_2$PH$_4$.2HCl to give the monocation:
δ1.33 (6H, s, C6-(CH$_3$)$_2$)
δ3.30 (1H, s, C7-H axial)
δ3.47 (1H, s, C7-H eq) in 6N DCl:
δ1.52 (6H, s, C6-(CH$_3$)$_2$)
δ3.53 (2H, s, C7-H$_2$)

The assignment of axial and equatorial of the monocation in (CD$_3$)$_2$SO is based on the work of Weber and Viscontini, *Helv. Chim. Acta*, 58 1772–1780 (1975).

$^{15}$N-NMR spectra were acquired on a Bruker WM-500 on a 0.5M solution of the dication in (CH$_3$)$_2$SO/10% (CD$_3$)$_2$SO.
δ133.8 (NI)
δ100.3 (NH$_2$)
δ78.8 (N8)
δ63.9 (N5)

All resonances, except that at δ133.8, were negative. Assignments were made by comparison to spectra published for 6-methyl- and 6,7-dimethyl-5,6,7,8-tetrahydropterin. The inability to detect N3 is most likely due to a counteractive NOE resulting from chemical shift anisotropy induced by the higher field compared to that used for the published spectra.

Mass spectrum. The mass spectrum of 6,6-Me$_2$PH$_4$ 2HCl, obtained by direct insertion, gave a parent peak at m/e 195 (80% relative abundance). There were two major fragments; one at m/e 180, which was also the base peak, from loss of one methyl, and the other at m/e 165 (50% relative abundance) due to loss of both methyl groups.

Stability. The rate of air oxidation of 6,6-Me$_2$PH$_4$ was measured in 0.1M Tris.HCl, pH 7.4 at 27°, i.e., enzyme assay conditions. The half-life was 23 min with a pseudo first order rate constant of 0.03 min$^{-1}$. This is similar to the constant previously determined for 6,7-Me$_2$PH$_4$.

Chemical Properties of Quinoid-6,6-dimethyldihydropterin

Quinoid-6,6-Me$_2$PH$_2$ is an intermediate in the synthesis of 6,6-Me$_2$PH$_4$ (see above). It can also be prepared quantitatively by bromine oxidation of 6,6-Me$_2$PH$_4$. The properties of q-6,6-Me$_2$PH$_2$ were determined on material made by the latter route. 6,6-Me$_2$PH$_4$ dihydrochloride, 0.1 mmoles, was dissolved in 3 ml methanol, and 22 mg Br$_2$ (0.14 mmoles) was added. Removal of solvent by rotary evaporation left a dark orange film. The sample was repeatedly redissolved in 3 ml fresh methanol and evaporated to dryness for a total of 6 times, until the film was light yellow and no odor of bromine could be detected. Failure to remove the excess bromine resulted in complex absorbance changes that hindered spectral studies of q-6,6-Me$_2$PH$_2$. The quantitative yield was established by reduction back to 6,6-Me$_2$PH$_4$ using 2-mercaptoethanol, which resulting in full recovery of the original material.

Ionic form of q-6,6-Me$_2$PH$_2$ at neutral pH

The molecular form was determined by analysis for counter ion. The dihydrochloride salt of 6,6-Me$_2$PH$_4$ was converted to the dihydrobromide salt by repeated precipitation from methanol-concentrated HBr with several volumes of ether. A methanolic solution of this material was oxidized with bromine and repeatedly rotary evaported, as above. A 40 mM solution of the resulting quinoid in methanol (2.5 ml) was titrated with 1.0N NaOH until a sample diluted 10-fold in water reached pH 6.5. The precipitate which formed was centrifuged and briefly suspended in cold water, recentrifuged, and completely dissolved in 20 ml methanol. HPLC analysis by a method adapted from Skelly, Anal. Chem., 54, 712–715, (1982), utilizing Spherisorb-C$_6$, 5 micron (25×0.46 cm), eluted with 10 mM nonylamine plus H$_3$PO$_4$ to pH 6.2, with detection at 205 nm, showed that the precipitate contained no bromide ion, as compared to KBr standards, and was, therefore, most likely the neutral species.

pKa. The pKa for the transition between the neutral and monocationic species of q-6,6-Me$_2$PH$_2$ was determined spectrophotometrically. A concentrated stock solution of quinoid, free of elemental bromine, in n-propanol was diluted to 0.1 mM into a series of sodium succinate buffers at constant ionic strength (I=0.01). Spectra, background corrected for each buffer individually, were acquired on a Perkin-Elmer 552 spectrophotometer thermostated to 25° C. The pKa was found to be 5.15±0.05.

UV. UV spectra were taken of the neutral species of q-6,6-Me$_2$PH$_2$ (pH 7.4) and of the monocation (pH 3.0) (FIGURE). The extinction coefficients, summarized in Table II, are based on quantitative conversion of standardized 6,6-Me$_2$PH$_4$ to q-6,6-Me$_2$PH$_2$ (see above).

TABLE II

| pH | Buffer | λ | Em(M−1cm−1) |
|---|---|---|---|
| 7.4 | 0.01 M Tris.HCl | 303 max | 8,400 |
| | | 245 max | 7,500 |
| | | 268 min | 4,900 |
| | | 340 shoulder | 4,300 |
| 3.0 | 0.01 M ammonium phosphate | 335 max | 4,800 |
| | | 253 max | 9,500 |
| | | 302 min | 3,400 |

NMR. $^1$H-NMR spectra were taken of q-6,6-Me$_2$PH$_2$. (1) On the hydrobromide salt in (CD$_3$)$_2$SO with a 60 MHz spectrometer:
δ1.32 (6H, s, C6-(CH$_3$)$_2$)
δ3.45 (2H, s, C7-H2) and (2) in D$_2$O (pD 7.0) with the 500 mHz spectrometer:
δ1.20 (6H, s, C6-(CH$_3$)$_2$)
δ3.29 (2H, s, C7-H$_2$)

Stability. The decay of q-6,6-Me$_2$PH$_2$ in a variety of environments was monitored spectrophotometrically. In contrast to quinoid dihydropterin monosubstituted at C6, and the 6-aminomethyl-6-methyl compound, q-6,6-Me$_2$PH$_2$ does not appear to rearrange to a 7,8-dihydropterin. In water, a plateau of highest stability is observed near neutral pH. At pH 6.8, solutions kept on ice have a half-life greater than 100 hours. In 0.1M Tris.HCl at pH 7.4 a half-life of 4 hours and 1.25 hours at 27° C. and 37° C., respectively, is observed. Loss of quinoid is somewhat increased in acid and greatly accelerated in base. At all pH's the disappearance of pteridine-like absorption suggests that a major ring rearrangement is occurring. This process is not affected by the presence of oxygen.

The half-life of q-6,6-Me$_2$PH$_2$ in aerated (CH$_3$)$_2$SO at ambient temperature is approximately 48 hours, and several weeks at −80° C. The generally increased stability in nonaqueous solvent indicates that decomposition in water may be dependent on an initial hydration.

The dry powder prepared from 6,6-Me$_2$PH$_4$, as outlined above, has been stored dessicated for several months at −80° C. with no detectable change.

TABLE III

Stability of Quinoid-6,6-Me$_2$PH$_2$ as a Function of pH, Temperature and Oxygen[a]

| pH | Temp | | t ½ (hours) |
|---|---|---|---|
| 7.4 | 27° C. | air | 4 |
| 7.4 | 37° C. | air | 1.25 |
| 7.4 | 37° C. | argon | 1.25 |
| 0 | 37° C. | air | 0.75 |
| 0 | 37° C. | argon | 0.75 |
| 6.8 | 0° C. | air | 104 |

[a]The rates of decomposition were determined from the absorption spectra in 1N HCl (pH 0), or Tris-MES (pH 6.8) or Tris.HCl (pH 7.4) each at 0.1 M.

Non-Enzymatic Reduction of Quinoid-6,6-Me$_2$PH$_2$ under Physiological Conditions Aromatic amino acid hydroxylase cofactor analogs which are relatively stable in the quinoid-dihydro form may have therapeutic potential for treatment of dihydropteridine reductase deficiency. Thus, it was of interest to determine the rate at which quinoid is reduced to the tetrahydropterin by various physiological reducing agents. Rates were measured in 0.1M Tris.HCl, pH 7.4 at 37°, from the decrease in absorbance at 340 nm. A reaction first order in each component was observed. With NADH, NADPH and absorbic acid, the rate of reduction (k=660 M$^{-1}$min$^{-1}$) was the same. The rate with cysteine was about four times slower (k=160 M$^{-1}$min$^{-1}$).

Example II: Synthesis and Properties of 6-Phenyl-6-Methyl-Tetrahydropterin

2-Amino-6-(2-amino-2-phenylpropylamino)-4-hydroxy-5-nitropyrimidine monohydrochloride 2-Amino-6-chloro-4-hydroxy-5-nitropyrimidine (0.626 g; 3.0 mmole) was dissolved in 130 ml of refluxing absolute ethanol and 0.45 g of 1,2-diamino-2-phenylpropane free-base (3.0 mmole) was added all at once dissolved in 8 ml of absolute ethanol. The mixture was stirred and maintained at reflux as a light yellow precipitate formed. Analysis by HPLC at 30 minutes showed a marked slowing of the condensation after a little over one-half of the reactants had been consumed. (Partisil SCX column (25×0.46 cm) eluted with 0.1M ammonium hydroxide made to pH 3.3 with formic acid/methanol, 3:2 v/v). Completion of the reaction to within 97% utilization of the diamine was accomplished by addition of 3.6 ml of 1M triethylamine in absolute ethanol (3.6 mmole) followed by 0.063 g of the above pyrimidine, the reaction being refluxed an additional hour. After being kept overnight at −15° C. the majority of the somewhat gelatinous product was collected by centrifugation, washed with 10 ml cold ethanol, and finally, twice with 30 ml each of ethyl ether. A second crop of equal purity was collected after allowing the mother liquor supernate to stand for an additional 5 days at −15° C., and similarly washed. These materials dried under vacuum in the presence of $P_2O_5$ gave 0.97 g (0.889+0.081) of the monohydrochloride salt for a yield of 95% based upon diamine.

6-(2-Amino-2-phenylpropylamino)-2,5-diamino-4-hydroxypyrimidine hydrochloride salt The above 0.97 g of 2-amino-6-(2-amino-2-phenylpropylamino)-4-hydroxy-5-nitropyrimidine monohydrochloride (2.85 mmole) was dissolved in 30 ml of argonated N,N-dimethylformamide at 70° C. and 30 ml of water (at 70° C.) added carefully dropwise so as to create a heavily supersaturated solution which was further deaerated by bubbling with argon. Four pre-weighed aliquots of 0.56 g $Na_2S_2O_4$ (12.83 mmole total), were added one minute apart with vigorous stirring under a stream of argon. The final aliquot produced a clear nearly colorless solution, which was cooled on ice.

Barium chloride, 5.13 ml of 1M in water, was added to the chilled solution which was centrifuged. A further 1.28 ml of 1M barium chloride was added, the mixture recentrifuged, and the supernate decanted. The barium precipitate was washed with 10 ml of cold argon-deaerated water and this supernate added to the first. The combined supernates were rotary evaporated along with 4 ml of concentrated HCl at reduced pressure until only N,N-dimethylformamide remained (approximately 15 to 20 ml). This was kept at −15° C. for 1 hour and the resulting suspension filtered and washed with 2×10 ml of N,N-dimethylformamide. The combined filtrates were rotary evaporated under reduced pressure to a gum which was dissolved in 20 ml of methanol. This solution was deaerated with bubbling argon and centrifuged at 20,000× g for 5 min to remove a sulfurous colloid. A dilution of this clear light yellow solution in 0.1N HCl shows a λmax at 271 nm.

2-Amino-4-hydroxy-6-methyl-6-phenyl-quinoiddihydro-pteridine

The above solution of the hydrochloride salt of 6-amino-(2-amino-2-phenylpropylamino)-2,5-diamino-4-hydroxypyrimidine in 20 ml of methanol was cooled on ice and 5.5 ml of 0.5M $I_2$ in methanol (at room temperature) was added all at once with stirring, still on ice. After 30 seconds, 13 ml of 0.5M NaOH in water (precooled on ice) was added, so that the acidity was brought to between pH 1.5 and 2.0 as determined by test paper. After 3 minutes, 5.5 to 6.5 ml of 1M NaOH in water (at ambient) was added to bring the pH to between 7.0 and 7.5 as determined by test paper, and the solution brought to room temperature. A yellow precipitate of quinoid dihydropteridine formed, and after 10 min the suspension was recooled on ice, rotary evaporated to half the volume, and filtered. The precipitate was washed with 5 ml of cold water followed by 30 ml of ethyl ether to remove excess iodine. After being dried under vacuum in the presence of $P_2O_5$, a weight of 0.362 g was obtained (50% yield from 2-amino-6-(2-amino-2-phenylpropylamino)-4-hydroxy-5-nitropyrimidine monohydrochloride, 47% based on 1,2-diamino-2-phenylpropane). This material appeared to be free of any UV absorbing impurities as judged from reduction to 2-amino-4-hydroxy-6-methyl-6-phenyl-5,6,7,8-tetrahydropteridine (see below).

2-Amino-4-hydroxy-6-methyl-6-phenyl-5,6,7,8-tetrahydropteridine (6-Ph-6-MePH$_2$)

The above dry quinoid-dihydropteridine was reduced in near quantitative yield by addition of 0.5M 2-mercaptoethanol at room temperature, such that the final concentration of product was approximately 10 mM (an almost saturated solution at neutral pH). To obtain the pure dihydrochloride salt, this solution was rotary evaporated to an oil which was dissolved in 2M HCl in methanol and 4 volumes of ethyl ether added, and the precipitate collected by centrifugation and washed twice by resuspension in fresh ethyl ether, followed by centrifugation. The vacuum dried white powder showed greater than 99% purity on elution from a Spherisorb $C_6$ column (25×0.4 cm) with 20 mM ammonium hydroxide made to pH 3.3 with formic acid, 1.0 mM $Na_2$ EDTA/methanol, 70:30, monitored by UV absorbance either at 254 or 267 nm.

Example III: Interaction of 6,6-Disubstituted Pteridines with Enzymes

Cofactor Properties of 6,6-Dimethyltetrahydropterin with Phenylalanine Hydroxylase The cofactor properties of 6-methyl- and 6,7-dimethyltetrahydropterin are well-known. The kinetic constants for these cofactors are summarized in Table IV, lines 1–3. It can be seen that a methyl in place of dihydroxypropyl at the 6-position has little effect on the $V_{max}$ but decreases the affinity about 5-fold. A second methyl at the 7-position has no further effect on the binding but decreases the rate 4- to 5-fold.

TABLE IV

Apparent Michaelis Constants and Relative Maximum Velocity for 6,6-Dimethyltetrahydropterin as Cofactor for Rat Liver Phenylalanine Hydroxylase[a]

| Cofactor | Km' for Cofactor (mM) | Km' for Phenylalanine (mM) | Relative $V_{max}$ |
|---|---|---|---|
| 1-BH$_4$[c] | 0.021 ± 0.003 | [b]0.17 ± 0.07 | 1.0 |
| 6-MePH$_4$ | 0.1 ± 0.02 | 0.3 ± 0.02 | 0.77 |
| 6,7-Me$_2$PH$_4$[d] | 0.09 ± 0.01 | 0.8 ± 0.1 | 0.17 |
| 6,6-Me$_2$PH$_4$ | 0.066 ± 0.01 | 0.65 ± 0.1 | 0.17 |

[a]Apparent Km's for cofactor were measured at 1 mM phenylalanine, and those for phenylalanine at 0.2 mM cofactor. All reactions were at atmospheric oxygen and were run in 0.1 M Tris.HCl, pH 7.4, at 27° C.
[b]Sigmoidal Km curve with Hill coefficient = 2; all other Km curves were hyberbolic
[c]Data from Bailey and Ayling, J. Biol. Chem., 253, 1598–1605 (1978)
[d]Data from Ayling et al., Anal. Biochem., 51, 80–90 (1973)

The 6,6-dimethyl substituted tetrahydropterin was tested for cofactor activity in a standard phenylalanine hydroxylase assay in which both cofactor consumption and tyrosine formation were monitored. As can be seen from Tables IV and V, 6,6-dimethyltetrahydropterin functions as a cofactor and catalyzes a completely coupled reaction, in which one tyrosine is formed for each cofactor molecule consumed. An apparent Michaelis constant was determined at 1 mM phenylalanine and atmospheric oxygen with concentrations of 6,6-Me$_2$PH$_4$ ranging from 0.02-0.3 mM. The effect of a second methyl at the 6-position slightly increases the affinity for phenylalanine hydroxylase, since the apparent Km was two-thirds to three-quarters that of 6-methyl and 6,7-dimethyltetrahydropterin (Table IV). The apparent Km for phenylalanine, with 6,6-Me$_2$PH$_4$ at 0.2 mM, was 0.65 mM, which is intermediate between that observed for the 6-methyl and 6,7-dimethyl analogs under the same conditions. The maximum velocity of the reaction with 6,6-Me$_2$PH$_4$ is similar to that with the 6,7-dimethyl compound and about 6 times slower than with the natural cofactor (Table IV).

TABLE V

Stoichiometry of the Reaction of 6,6-Dimethyltetrahydropterin with Phenylalanine Hydroxylase[a]

| Initial [6,6-Me$_2$PH$_4$] (mM) | 6,6-Me$_2$PH$_4$ oxidized (nmoles) | Tyrosine produced (nmoles) | 6,6-Me2PH4 / tyrosine |
|---|---|---|---|
| 0.01 | 4.4 | 4.27 | 1.03 |
| 0.03 | 9.1 | 9.77 | 0.93 |
| 0.06 | 11.76 | 12.57 | 0.94 |
| 0.1 | 21.18 | 19.25 | 1.10 |

[a]Reactions were monitored spectrophotometrically at 340 nm for 2-3 minutes against a reference in which phenylalanine was omitted. The reaction was terminated with trichloroacetic acid, and the mixture assayed for tyrosine. Cofactor oxidized in the enzymatic reaction was calculated from the molar extinction coefficient of 3,600 M$^{-1}$cm$^{-1}$ for the conversion of 6,6-Me$_2$PH$_4$ to q-6,6-Me$_2$PH$_2$ at 340 nm. In determining the stoichiometry of the reaction directly, a cofactor regenerating system was not included. Thus the above do not represent initial rates, since the reaction does not remain linear with time.

Absorbance Spectrum of Quinoid-6,6-Me$_2$PH$_2$ Generated by Phenylalanine Hydroxylase Spectra were taken of the q-6,6-Me$_2$PH$_2$ synthesized enzymatically from 6,6-Me$_2$PH$_4$, and a comparison made with the chemically produced compound. The spectrophotometer was baseline corrected with sample and reference cuvettes containing all of the reaction components (0.1M Tris.HCl, pH 7.4, 4 mM phenylalanine, 2500 units catalase, 0.3 unit phenylalanine hydroxylase) except pterin in a total volume of 0.99 ml. 6,6-Me$_2$PH$_4$ (10 μl of 10 mM) was then added to the sample and distilled H$_2$O (10 μl) to the reference cuvette. Scanning was begun immediately and spectra taken at 2 minute intervals. The formation of q-6,6-Me$_2$PH$_2$ was complete within 4 minutes. After correction for tyrosine formed and phenylalanine consumed, the spectrum was within 3% of that produced by Br$_2$ oxidation of 6,6-Me$_2$PH$_4$ (FIGURE).

Spectrum of Quinoid-6,6-Me$_2$PH$_2$ Produced by Peroxidase

Sample and reference cuvettes contained 0.1M Tris.HCl, pH 7.4, 6 units peroxidase and 0.4 mM H$_2$O$_2$ in a total volume of 0.99 ml. Following baseline correction, 6,6-Me$_2$PH$_4$ (10 μl of 10 mM) was added to the sample, and H$_2$O (10 μl) to the reference. Scans taken immediately, and at 2 minute intervals, indicated that the quinoid was completely formed in a few seconds, with a spectrum identical to that of the chemically synthesized product (FIGURE).

Inhibition of Phenylalanine Hydroxylase by Dihydropterins

Inhibition by quinoid-dihydropterin: The cofactor properties of 6,6-Me$_2$PH$_4$ were utilized to investigate inhibition of phenylalanine hydroxylase by q-6,6-Me$_2$PH$_2$. In contrast to a more standard cofactor, electron exchange between the quinoid-dihydro and tetrahydro forms would not result in a change of concentration of either. Measurements were made under standard assay conditions with cofactor concentration varied between 0.05 and 0.3 mM. Stock solutions of 6,6-Me$_2$PH$_2$ were in 0.1M assay buffer. No inhibition of purified phenylalanine hydroxylase was observed with concentrations of freshly prepared q-6,6-Me$_2$PH$_2$ up to 0.4 mM.

Inhibition by 7,8-dihydropterins: For comparison, the inhibitory properties of 6-Me-7,8-PH$_2$ and 7,8-dihydrobiopterin were studied. Standard assay conditions, with 6-MePH$_4$ as cofactor over a range of 0.05 mM to 0.3 mM, were employed. Competitive inhibition was observed in both cases, with apparent KI's of 0.2 mM and 0.05 mM, respectively.

Substrate Properties of Quinoid-6,6-dimethyldihydropterin for Dihydropteridine Reductase 6,6-Dimethyltetrahydropterin was oxidized by three different procedures to produce q-6,6-Me$_2$PH$_2$ to be tested as a substrate for dihydropteridine reductase.

(i) Chemical synthesis. The quinoid was generated from 6,6-Me$_2$PH$_4$, as outlined previously. The q-6,6-Me$_2$PH$_2$ was dissolved in 0.1M Tris.HCl, pH 7.4 immediately before use to make a 10 mM stock solution, which was kept on ice. To test for substrate activity a small volume (<50 μl) was added to a cuvette containing 0.1M Tris.HCl, pH 7.4, which had been temperature equilibrated to 27°, and the absorbance at 340 nm was measured.

(ii) Oxidation by peroxidase and H$_2$O$_2$. Peroxidase (6 units/ml final volume) was temperature equilibrated in 0.1M Tris.HCl, pH 7.4, at 27° for 5 minutes. H$_2$O$_2$ (1.2 mM final concentration) was then added, followed by 6,6-Me$_2$PH$_4$. Conversion to q-6,6-Me$_2$PH$_2$, monitored at 340 nm, was complete within a few seconds.

(iii) Generation by phenylalanine hydroxylase: Phenylalanine hydroxylase (0.6 units/ml), catalase (2500 units/ml), and phenylalanine (3 mM final concentration) were temperature equilibrated at 27° in 0.1M Tris.HCl, pH 7.4. At 5 minutes, 6,6-Me$_2$PH$_4$ was introduced and monitored at 340 nm. Conversion of 6,6-Me$_2$PH$_4$ to quinoid dihydropterin was complete in 1-7 minutes, depending on the concentration. To each of the above solutions containing q-6,6-Me$_2$PH$_2$, NADH (final concentration 0.1 mM) as added, and the background rate recorded for 1 minute. Reaction was then initiated with dihydropteridine reductase (0.01 units/ml). Rates were calculated from the enzyme dependent decrease in O.D. at 340 nm, using an extinction coefficient of 9.8 for the chemically synthesized substrate and 6.2 for the peroxidase- and phenylalanine-hydroxylase-containing reactions in which the pterin is maintained in the quinoid form. Due to the high concentrations of q-6,6-Me$_2$PH$_2$ required to obtain an accurate Km, cuvettes of 0.5 cm light path were used.

The beef liver and sheep liver enzymes showed similar activities with q-6,6-Me$_2$PH$_2$. The Km measured in 0.1M Tris.HCl, pH 7.4, at 27° C., was above, as 0.4 mM for both enzymes. This Km was obtained regardless of the method of generation of the quinoid dihydropterin. The V$_{max}$'s were also the same for the dihydropteridine reductase catalyzed reduction of quinoid generated by any of the three methods (Table VI). Thus, the quinoid products of each procedure appear to behave equally.

At saturating concentrations, utilization of q-6,6-Me$_2$PH$_2$ by dihydropteridine reductase is comparable to the natural quinoid dihydrobiopterin and the commonly used synthetic substrates quinoid-6-methyl- and 6,7-dimethyl-dihydropterin. The V$_{max}$ of q-6,6-Me$_2$PH$_2$ is within a factor of two of the V$_{max}$ of any of these substrates (Table VI). However, the affinity for enzyme is significantly affected by the second methyl group at the 6-position. The Km is more than an order of magnitude higher than that for either of the two compounds with a single methyl at the 6-position and more than two orders of magnitude higher than that of the natural substrate. The Km of quinoid 6-phenyl-6-methyl PH$_2$ is considerably lower than that of q-6,6-Me$_2$PH$_2$, and approaches that of q-6-monomethyl PH$_2$. The V$_{max}$ of 6-phenyl-6-methyl is similar to that of q-dihydrobiopterin (TABLE VI).

TABLE VI

Michaelis Constant and Relative Maximum Velocity for Quinoid-6,6-Me$_2$PH$_2$ as Substrate for Sheep and Beef Liver Dihydropteridine Reductase[a]

| Quinoid Substrate | Method of Substrate Production | Km (mM) Beef | Km (mM) Sheep | Relative V$_{max}$ Beef | Relative V$_{max}$ Sheep |
|---|---|---|---|---|---|
| 6,6-Me$_2$PH$_2$ | Bromine oxidation | 0.4 | 0.4 | 1 | 1 |
| 6,6-Me$_2$PH$_2$ | Phe hydroxylase + phe | 0.4 | 0.4 | 1 | 1 |
| 6,6-Me$_2$PH$_2$ | Peroxidase + H$_2$O$_2$ | 0.4 | — | 1 | — |
| 6-MePH$_2$ | Peroxidase + H$_2$O$_2$ | 0.03 | — | 1.5 | — |
| 6,7-Me$_2$PH$_2$ | Peroxidase + H$_2$O$_2$ | — | 0.03 | — | 2 |
| 6-Ph-6-MePH$_2$ | Peroxidase + H$_2$O$_2$ | 0.07 | — | 0.6 | — |
| dihydrobiopterin (natural isomer) | Peroxidase + H$_2$O$_2$ | 0.004 | 0.004 | 0.5 | 0.5 |

[a]The concentration of NAD was 0.1 mM; Km for NADH <0.005 mM in all cases.

Cofactor Activity of Tetrahydrobiopterin Analogs with Tyrosine Hydroxylase

Various analogs of tetrahydrobiopterin were tested for activity with tyrosine hydroxylase in a manner similar to that described above for phenylalanine hydroxylase. The results are summarized in Table VII.

TABLE VII

Cofactor Activity of Tetrahydrobiopterin Analogs with Tyrosine Hydroxylase

| Cofactor | Km | Rel. Vmax | Rel Vmax / Km |
|---|---|---|---|
| Tetrahydrobiopterin | | | 1 |
| 6-Methyl-PH$_4$ | 1.4 mM | 4.5 | 3 |
| 6,6-Dimethyl-PH$_4$ | 0.4 mM | 1 | 3 |
| 6-Phenyl-PH$_4$ | 0.33 mM | 10 | 30 |

TABLE VII-continued

Cofactor Activity of Tetrahydrobiopterin Analogs with Tyrosine Hydroxylase

| Cofactor | Km | Rel. Vmax | Rel Vmax / Km |
|---|---|---|---|
| 6-Phenyl-6-Methyl-PH$_4$ | 0.7 mM | 2 | 3 |

Rel Vmax / Km gives the ratio of rates when cofactor concentration is much lower than Km as will be the case within the brain and indicates expected increased activity for the analogs. However, the 6-monosubstituted compounds are not expected to achieve this higher activity because of their previously discussed tendency to rearrange to 7,8-dihydro forms, a tendency that is blocked in the 6,6-disubstituted compounds.

Example IV: In Vivo Testing

Preliminary in vivo testing of 6,6-disubstituted pteridines has been conducted. 6,6-Dimethyltetrahydropterin was injected intraperitoneally into mice at a dose rate of 0.1 μmole/g body weight. Maximum brain concentration was reached about one hour after injection and was more than 30 times higher than the maximum level reached by tetrahydrobiopterin injected in a similar manner.

The invention now being fully described, it will be apparent to one of ordinary skill in the art that many changes and modifications can be made thereto without departing from the spirit or scope of the invention as set forth herein.

We claim:

1. A method of synthesizing quinoid 6,6-disubstituted dihydropteridines which comprises the steps of:
   (a) addition of an oxidant selected from the group consisting of bromine, iodine, hypochlorite, ferricyanide, bromate, iodate, periodate, or dichlorophenol-indophenol to a solution of a 6-(2'-amino-2',2'-disubstituted-ethylamino)-5-amino-pyrimidine of the formula (XIX) in an acidic medium comprising a mixture of nonaqueous solvent and water, said water being in an amount between one mole of water per mole of said 6-(2'-amino-2',2'-disubstituted-ethylamino)-5-amino-pyrimidine and 33% of the total volume of said medium, whereby a 5-imino-quinoid pyrimidine is formed;

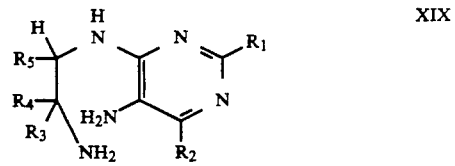

(b) adjusting the pH of said acidic medium to between pH 1 and pH 3 after said addition of an oxidant, whereby hydrolysis of said 5-imino-quinoid pyrimidine occurs;
   (c) neutralizing said acidic medium, whereby intramolecular condensation occurs to give said quinoid 6,6-disubstituted dihydropteridine;
wherein R$_1$ and R$_2$ are the same or different and represent
   (1) hydrogen;
   (2) hydroxy;
   (3) alkoxy of 1 to 4 carbon atoms;
   (4) amino of the formula —NR$_6$R$_7$, wherein R$_6$ and R$_7$ are the same or different and represent
      (a) hydrogen;
      (b) alkyl of 1 to 4 carbon atoms; or (c) cycloalkyl of 3 to 6 carbon atoms;
(5) cycloamino selected from
   (a) aziridino,
   (b) azetidino,
   (c) pyrrolidino,
   (d) piperidino, and
   (e) morpholino, wherein said cycloamino is attached to the pyrimidine ring of said formula through a nitrogen of said cycloamino;
(6) alkylthio of 1 to 3 carbons; or
(7) benzylthio;
with the provision that not more than one of $R_1$ and $R_2$ is hydrogen; $R_3$ and $R_4$ are the same or different and represent
   (1) alkyl of 1 to 12 carbon atoms;
   (2) alkenyl of 2 to 7 carbon atoms;
   (3) alkynyl of 2 to 7 carbon atoms;
   (4) cycloalkyl, saturated or unsaturated, of 3 to 10 carbon atoms with 3 to 7 atoms in the ring;
   (5) bicycloalkyl, saturated or unsaturated, of 6 to 13 carbon atoms with 4 to 7 atoms per ring;
   (6) adamantyl;
   (7) alkyl of 1 to 12 carbon atoms or alkenyl of 2 to 7 carbon atoms, substituted with 1, 2, 3 or 4 of hydroxy, protected amino, oxo, or thio; phosphate, or fluoro, with the proviso that when the number of carbons is greater than one the number of substituents is no greater than the number of carbon atoms in $R_3$ or $R_4$;
   (8) aryl, wherein aryl is phenyl or naphthyl;
   (9) arylalkyl of 7 to 13 carbon atoms;
   (10) aryl or arylalkyl substituted with 1, 2, or 3 alkyl of 1 to 4 carbon atoms, trifluoromethyl, hydroxy, alkoxy of 1 to 4 carbon atoms, fluoro, chloro, bromo, amino, methylamino, or dimethylamino in the aryl group;
   (11) thienyl, thienylmethyl;
   (12) furyl, furylmethyl;
   (13) tetrahydrofuryl;
   (14) pyridyl, pyridylmethyl;
   (15) pyridyl substituted with 1, 2, or 3 alkyl of 1 to 4 carbon atoms, amino, hydroxy, chloro, or fluoro;
   (16) a group consisting of

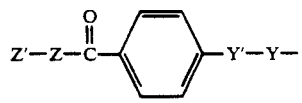

wherein Y is methylene or ethylene either of which is unsubstituted or is substituted with 1 or 2 substituents selected from fluoro, chloro, and methyl; Y' is
   (a) —$NR_{10}$—, wherein $R_{10}$ is hydrogen; formyl; formimino; hydroxymethyl; alkyl of 1 to 3 carbon atoms; or alkenyl or alkynyl of 2 to 3 carbon atoms,
   (b) —O—, or
   (c) —S—; and
ZZ' is OH, $C_1$-$C_4$ alkoxy, $NH_2$, or an amino acid residue of the formula ZZ wherein ZZ represents the residue of an amino acid or amino acid polymer of the formula

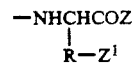

wherein Z represents OH, $C_1$-$C_4$ alkyloxy, or $NH_2$, R represents a divalent alkyl radical of 1 to 5 carbons, and $Z^1$ represents protected $NH_2$ or $COZ^2$ where $Z^2$ is Z or the residue of an amino acid or amino acid polymer of the formula

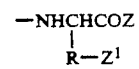

where the total number of amino acid residues in ZZ does not exceed 7 and each Z, R, $Z^1$ and $Z^2$ operates independently in defining ZZ;
(17) carboxyl, or
(18)

wherein $R_{12}$ is a 1- to 22-carbon alkyl or alkenyl group; and $R_5$ is
   (1) hydrogen,
   (2) alkyl of 1 to 6 carbon atoms,
   (3) cycloalkyl of 3 to 7 carbon atoms,
   (4) phenyl, phenylmethyl,
   (5) alkoxy of 1 to 4 carbon atoms, or
   (6) carboxyl;
with the provisions that (i) $R_3$ and $R_4$ together may form a 3- to 7-carbon spiro alkyl ring, with carbon 6 of the pteridine ring being the spiro carbon; (ii) $R_4$ and $R_5$ together may form a 5- or 6-membered carbocyclic ring fused to pteridine carbons 6 and 7.

2. The method of claim 1, wherein said oxidant is selected from the group consisting of iodine, ferricyanide, or dichlorophenol-indophenol.

3. The method of claim 1, wherein said oxidant is bromine.

4. The method of claim 1, wherein said neutralizing is by addition of a base to about pH 7.

* * * * *